United States Patent
Fjield et al.

(10) Patent No.: US 7,326,201 B2
(45) Date of Patent: Feb. 5, 2008

(54) THERMAL TREATMENT METHODS AND APPARATUS WITH FOCUSED ENERGY APPLICATION

(75) Inventors: Todd Fjield, Laguna Hills, CA (US); Edward Paul Harhen, Duxbury, MA (US); David E. Acker, St. James, NY (US); Patrick David Lopath, Stamford, CT (US)

(73) Assignee: ProRhythm, Inc., Ronkonkoma, NY (US)

( * ) Notice: Subject to any disclaimer, the term of this patent is extended or adjusted under 35 U.S.C. 154(b) by 45 days.

(21) Appl. No.: 11/228,575

(22) Filed: Sep. 16, 2005

(65) Prior Publication Data

US 2006/0009753 A1  Jan. 12, 2006

Related U.S. Application Data

(60) Continuation of application No. 10/227,092, filed on Aug. 23, 2002, now Pat. No. 7,083,614, which is a division of application No. 09/905,227, filed on Jul. 13, 2001, now Pat. No. 6,635,054.

(60) Provisional application No. 60/218,641, filed on Jul. 13, 2000.

(51) Int. Cl.
*A61B 18/04* (2006.01)
*A61N 7/02* (2006.01)

(52) U.S. Cl. .................... 606/27; 606/28; 600/459; 600/462; 601/2; 601/3

(58) Field of Classification Search .......... 606/27–28; 607/96, 122, 101; 600/459–469, 446, 439, 600/373–375, 470; 601/2–3
See application file for complete search history.

(56) References Cited

U.S. PATENT DOCUMENTS

| | | | |
|---|---|---|---|
| 3,168,659 | A | 2/1965 | Bayre et al. |
| 4,084,582 | A | 4/1978 | Nigam |
| 4,185,501 | A | 1/1980 | Nigam |
| 4,194,510 | A | 3/1980 | Proudian |
| 4,387,720 | A | 6/1983 | Miller |
| 4,391,281 | A | 7/1983 | Green |
| 4,433,692 | A | 2/1984 | Baba |

(Continued)

FOREIGN PATENT DOCUMENTS

EP  1042990  10/2000

(Continued)

OTHER PUBLICATIONS

Chen, Shih-Ann, M.D., "Initiation of Atrial Fibrillation by Ectopic Beats Originating From the Pulmonary Veins," Circulation 100 (18):1879-86, 1999.

(Continued)

*Primary Examiner*—Roy D. Gibson
(74) *Attorney, Agent, or Firm*—Lerner, David, Littenberg, Krumholz & Mentlik, LLP

(57) ABSTRACT

A collapsible ultrasonic reflector incorporates a gas-filled reflector balloon, a liquid-filled structural balloon an ultrasonic transducer disposed within the structural balloon. Acoustic energy emitted by the transducer is reflected by a highly reflective interface between the balloons. In a cardiac ablation procedure, the ultrasonic energy is focused into an annular focal region to ablate cardiac tissue extending in an annular path along the wall. Devices for stabilizing the balloon structure and for facilitating collapse and withdrawal of the balloon structure are also disclosed.

17 Claims, 15 Drawing Sheets

U.S. PATENT DOCUMENTS

| | | | |
|---|---|---|---|
| 4,643,186 A | 2/1987 | Rosen et al. |
| 4,672,961 A | 6/1987 | Davies |
| 4,680,499 A | 7/1987 | Umemura et al. |
| 4,685,334 A | 8/1987 | Latimer |
| 4,691,714 A | 9/1987 | Wong et al. |
| 4,722,347 A | 2/1988 | Abrams et al. |
| 4,800,316 A | 1/1989 | Ju-Zhen |
| 4,841,977 A | 6/1989 | Griffith et al. |
| 4,842,977 A | 6/1989 | Griffith et al. |
| 4,869,263 A | 9/1989 | Segal et al. |
| 4,914,510 A | 4/1990 | Proudian |
| 4,945,912 A | 8/1990 | Langberg |
| 4,972,826 A | 11/1990 | Koehler et al. |
| 5,104,393 A | 4/1992 | Isner |
| 5,105,116 A | 4/1992 | Okamoto et al. |
| 5,117,831 A | 6/1992 | Jang et al. |
| 5,135,001 A | 8/1992 | Sinofsky et al. |
| 5,140,987 A | 8/1992 | Schuger |
| 5,160,336 A | 11/1992 | Favre |
| 5,167,233 A | 12/1992 | Eberle et al. |
| 5,209,299 A | 5/1993 | Ayres |
| 5,217,454 A | 6/1993 | Khoury |
| 5,226,421 A | 7/1993 | Frisbie et al. |
| 5,226,430 A | 7/1993 | Spears |
| 5,240,005 A | 8/1993 | Viebach |
| 5,242,438 A | 9/1993 | Saadatmanesh et al. |
| 5,242,441 A | 9/1993 | Avitall |
| 5,246,438 A | 9/1993 | Langberg |
| 5,281,213 A | 1/1994 | Milder et al. |
| 5,281,218 A | 1/1994 | Imran |
| 5,293,868 A | 3/1994 | Nardella |
| 5,295,484 A | 3/1994 | Marcus et al. |
| 5,305,731 A | 4/1994 | Buchholtz |
| 5,305,755 A | 4/1994 | Nakao |
| 5,348,010 A | 9/1994 | Schnall et al. |
| 5,364,388 A | 11/1994 | Koziol |
| 5,385,148 A | 1/1995 | Lesh et al. |
| 5,415,654 A | 5/1995 | Daikuzono |
| 5,419,335 A | 5/1995 | Hartmann et al. |
| 5,421,338 A | 6/1995 | Seyed-Bolorforosh |
| 5,423,319 A | 6/1995 | Seyed-Bolorforosh |
| 5,423,807 A | 6/1995 | Milder |
| 5,454,782 A | 10/1995 | Perkins |
| 5,468,239 A | 11/1995 | Tanner |
| 5,471,988 A | 12/1995 | Fujio |
| 5,477,736 A | 12/1995 | Lorraine |
| 5,488,955 A | 2/1996 | Dias |
| 5,513,639 A | 5/1996 | Satomi et al. |
| 5,575,766 A | 11/1996 | Swartz et al. |
| 5,575,787 A | 11/1996 | Abela |
| 5,582,609 A | 12/1996 | Swanson et al. |
| 5,596,989 A | 1/1997 | Morita |
| 5,606,974 A | 3/1997 | Castellano |
| 5,620,479 A | 4/1997 | Diedrich |
| 5,630,837 A | 5/1997 | Crowley |
| 5,655,539 A | 8/1997 | Wang et al. |
| 5,676,692 A | 10/1997 | Sanghui |
| 5,767,692 A | 10/1997 | Sanghui |
| 5,693,043 A | 12/1997 | Kittrell |
| 5,704,361 A | 1/1998 | Seward et al. |
| 5,707,352 A | 1/1998 | Sekins et al. |
| 5,720,287 A | 2/1998 | Chapelon et al. |
| 5,762,066 A | 6/1998 | Law et al. |
| 5,817,018 A | 10/1998 | Ohtomo |
| 5,840,031 A | 11/1998 | Crowley |
| 5,840,066 A | 11/1998 | Swanson |
| 5,848,969 A | 12/1998 | Panescu et al. |
| 5,860,974 A | 1/1999 | Abele |
| 5,916,170 A | 6/1999 | Kolz et al. |
| 5,916,213 A | 6/1999 | Haissaguerre et al. |
| 5,921,982 A | 7/1999 | Lesh et al. |
| 5,931,811 A | 8/1999 | Haissaguerre |
| 5,938,660 A | 8/1999 | Swartz et al. |
| 5,964,751 A | 10/1999 | Amplatz |
| 5,971,983 A | 10/1999 | Lesh |
| 6,002,955 A | 12/1999 | Willems |
| 6,004,269 A | 12/1999 | Crowley et al. |
| 6,012,457 A | 1/2000 | Lesh |
| 6,013,053 A | 1/2000 | Bower et al. |
| 6,022,319 A | 2/2000 | Willard |
| 6,024,740 A | 2/2000 | Lesh et al. |
| 6,055,859 A | 5/2000 | Kozuka et al. |
| 6,064,902 A | 5/2000 | Haissaguerre |
| 6,068,629 A | 5/2000 | Haissaguerre et al. |
| 6,071,279 A | 6/2000 | Whayne |
| 6,094,988 A | 8/2000 | Aindow |
| 6,106,474 A | 8/2000 | Koger et al. |
| 6,117,101 A | 9/2000 | Diederich et al. |
| 6,123,456 A | 9/2000 | Lyons |
| 6,146,379 A | 11/2000 | Fleischman |
| 6,152,144 A | 11/2000 | Lesh et al. |
| 6,152,920 A | 11/2000 | Thompson |
| 6,161,543 A | 12/2000 | Cox et al. |
| 6,163,716 A | 12/2000 | Edwards |
| 6,164,283 A | 12/2000 | Lesh |
| 6,190,382 B1 | 2/2001 | Ormsby |
| 6,193,713 B1 | 2/2001 | Geistert et al. |
| 6,196,059 B1 | 3/2001 | Kosslinger et al. |
| 6,197,023 B1 | 3/2001 | Muntermann |
| 6,200,269 B1 | 3/2001 | Lin et al. |
| 6,200,315 B1 | 3/2001 | Gaiser et al. |
| 6,203,525 B1 | 3/2001 | Whayne et al. |
| 6,203,531 B1 | 3/2001 | Ockuly et al. |
| 6,206,831 B1 | 3/2001 | Suorsa |
| 6,212,426 B1 | 4/2001 | Swanson |
| 6,231,561 B1 | 5/2001 | Frazier |
| 6,235,025 B1 | 5/2001 | Swartz et al. |
| 6,237,605 B1 | 5/2001 | Vaska et al. |
| 6,241,754 B1 | 6/2001 | Swanson et al. |
| 6,245,064 B1 | 6/2001 | Lesh et al. |
| 6,251,109 B1 | 6/2001 | Hassett et al. |
| 6,254,599 B1 | 7/2001 | Lesh et al. |
| 6,280,402 B1 | 8/2001 | Ishibashi et al. |
| 6,282,949 B1 | 9/2001 | Axelsson |
| 6,283,127 B1 | 9/2001 | Sterman et al. |
| 6,290,674 B1 | 9/2001 | Roue et al. |
| 6,305,378 B1 | 10/2001 | Lesh |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,778 B1 | 11/2001 | Gambale et al. |
| 6,330,473 B1 | 12/2001 | Swanson et al. |
| 6,332,880 B1 | 12/2001 | Yang et al. |
| 6,383,151 B1 | 5/2002 | Diederich et al. |
| 6,398,792 B1 | 6/2002 | O'Connor |
| 6,461,314 B1 | 10/2002 | Pant et al. |
| 6,492,762 B1 | 12/2002 | Pant et al. |
| 6,500,174 B1 | 12/2002 | Maguire et al. |
| 6,513,385 B1 | 2/2003 | Han et al. |
| 6,517,536 B2 | 2/2003 | Hooven et al. |
| 6,543,271 B2 | 4/2003 | Herrmann et al. |
| 6,641,579 B1 | 11/2003 | Bernardi et al. |
| 6,642,515 B1 | 11/2003 | Yamaguchi |
| 6,652,515 B1 | 11/2003 | Maguire et al. |
| 2001/0007070 A1 | 7/2001 | Stewart et al. |
| 2002/0065512 A1 | 5/2002 | Fjield et al. |
| 2003/0050637 A1 | 3/2003 | Maguire et al. |

FOREIGN PATENT DOCUMENTS

| | | |
|---|---|---|
| JP | 10-127678 | 5/1998 |
| JP | 11-218100 | 8/1999 |
| WO | WO-90/00420 | 1/1990 |
| WO | WO-98/41178 | 9/1998 |

| | | |
|---|---|---|
| WO | WO-98/49957 | 11/1998 |
| WO | WO-98/52465 | 11/1998 |
| WO | WO-99/02096 | 1/1999 |
| WO | WO-99/44519 | 9/1999 |
| WO | WO-99/52423 | 10/1999 |
| WO | WO-99/56812 | 11/1999 |
| WO | WO-00/16850 | 3/2000 |
| WO | WO-00/27292 | 5/2000 |
| WO | WO-00/42934 | 7/2000 |
| WO | WO-00/51511 | 9/2000 |
| WO | WO-00/51683 | 9/2000 |
| WO | WO-00/56237 | 9/2000 |
| WO | WO-00/67648 | 11/2000 |
| WO | WO-00/67656 | 11/2000 |
| WO | WO-00/67830 | 11/2000 |
| WO | WO-00/67832 | 11/2000 |

OTHER PUBLICATIONS

Chinitz, Larry A., "Mapping Reentry Around Atriotomy Scars Using Double Potentials," 1996.

Cosio, Francisco G., "Atrial Flutter Mapping and Ablation II," Pacing & Clin. Electrophysiol. 19(6):965-75, 1996.

Feld, Gregory K., "Radiofrequency Catheter Ablation for the Treatment of Human Type I Atrial Flutter," 1992.

Fjield, et al., U.S. Appl. No. 60/218,641, filed Jul. 13, 2000.

Gallagher, John J., "Wolff-Parkinson-White Syndrome: Surgery to Radiofrequency Catheter Ablation," 1997.

Haissaguerre, Michel, "Electrophysiological End Point for Catheter Ablation of Atrial Fibrillation Initiated From Multiple Venous Foci," 1999.

Haissaguerre, Michel, M.D., "Predominant Origin of Atrial Panarrythmic Triggers in the Pulmonary Veins: A Distinct Electrophysiologic Entity," 1997.

Haissaguerre, Michel, M.D., "Radiofrequency Catheter Ablation in Unusual Mechanisms of Atrial Fibrillation," 1994.

Haissaguerre, Michel, M.D., "Right and Left Atrial Radiofrequency Catheter Therapy of Paroxysmal Atrial Fibrillation," 1996.

Haissaguerre, Michel, M.D., "Spontaneous Initiation of Atrial Fibrillation by Ectopic Beats Originating in the Pulmonary Veins," 1998.

Hatala, Robert, "Radiofrequency Catheter Ablation of Left Atrial Tachycardia Originating Within the Pulmonary Vein in a Patient with Dextrocardia," 1996.

Hocini, Meleze, "Concealed Left Pulmonary Vein Potentials Unmasked by Left Atrial Stimulation," 2000.

Hocini, Meleze, "Multiple Sources Initating Atrial Fibrillation from a Single Pulmonary Vein Identified by a Circumferential Catheter," 2000.

Hsieh, Ming-Hsiung, M.D., "Double Multielectrode Mapping Catheters Facilitate Radiofrequency Catheter Ablation of Focal Atrial Fibrillation Originating from Pulmonary Veins," 1998.

Jais, Pierre, M.D., "A Focal Source of Atrial Fibrillation Treated by Discrete Radiofrequency Ablation," 1996.

Kay, G. Neal, "Radiofrequency Ablation for Treatment of Primary Atrial Tachycardia," 1993.

Krimholtz et al., "New Equivalent Circuits for Elementary Piezoeletric Transducers," Electronics Lettres, vol. 6, No. 13, pp. 398-399, Jun. 25, 1970.

Kumagai, Koichiro, "Treatment of Mixed Atrial Fibrillation and Typical Atrial Flutter by Hybrid Catheter Ablation," 2000.

Lesh, M.D., "An Anatomic Approach to Prevention of Atrial Fibrillation: Pulmonary Vein Isolation with Through-the-Balloon Ultrasound Ablation (TTB-US)," Thorac. Cardiovasc. Surg. 47 (1999) (Suppl.) 347-51.

Lesh, Michael D., M.D., "Radiofrequency Catheter Ablation of Atrial Arrhythmias," 1994.

Liem, L. Bing, "In Vitro and In Vivo Results of Transcatheter Microwave Ablation Using Forward-Firing Tip Antenna Design," 1996.

Lin, Wei-Shiang, M.D., "Pulmonary Vein Morphology in Patients with Paroxysmal Atrial Fibrillation Initiated by Ectopic Beats Originating From the Pulmonary Veins," Circulation 101(11):1274-81, 2000.

Mallavarapu, Christopher, "Radiofrequency Catheter Ablation of Atrial Tachycardia with Unusual Left Atrial Sites of Origin," 1996.

Montenero, Sandro, Annibale, "Electrograms for Identification of the Atrial Ablation Site During Catheter Ablation of Accessory Pathways," 1996.

Moubarak, Jean B., "Pulmonary Veins-Left Atrial Junction: Anatomic and Histological Study," Pacing & Clin. Electrophys. 23(11 Pt. 2):1836-8, 2000.

O'Connor, Brian K., "Radiofrequency Ablation of A Posteroseptal Accessory Pathway Via the Middle Cardia Vein in a Six-Year Old Child," 1997.

Prager, Nelson, A., "Long Term Effectiveness of Surgical Treatment of Ectopic Atrial Tachycardia," 1993.

Reuter, David, M.D., "Future Directions of Electrotherapy for Atrial Fibrilation," 1997.

Robbins, Ivan, M.D., "Pulmonary Vein Stenosis After Catheter Ablation of Atrial Fibrillation," 1998.

Scheinman, Melvin M., "NASPE Survey on Catheter Ablation," 1995.###.

Swartz, John F., "A Catheter-based Curative Approach to Atrial Fibrillation in Humans," 1994.

Swartz, John F., M.D., "Radiofrequency Endocardial Catheter Ablation of Accessory Atrioventricular Pathway Atrial Insertion Sites," 1993.

Tracy, Cynthia M., "Radiofrequency Catheter Ablation of Ectopic Atrial Tachycardia Using Paced Activation Sequence Mapping," J. of the Amer. College of Cardiol. 21(4):910-7, 1993.

Van Hare, George F., "Radiofrequency Catheter Ablation of Supraventricular Arrhythmias in Patients With Congenital Heart Disease: Results and Technical Considerations," J. of the Amer. College of Cardiol. 22(3):883-90, 1993.

Volkmer, Marius, M.D., "Focal Atrial Tachycardia from Deep Inside the Pulmonary Veins," 1997.

Walsh, Edward P., M.D., "Transcatheter Ablation of Ectopic Atrial Tachycardia in Young Patients Using Radiofrequency Current," 1992.

Zipes, Douglas P., M.D., "Catheter Ablation of Arrhythmias," 1994.

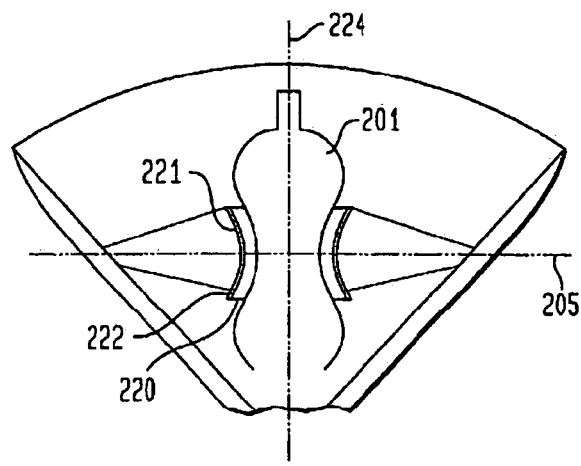
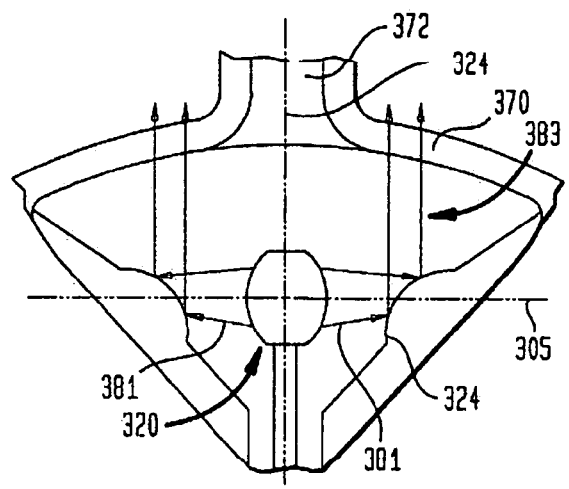
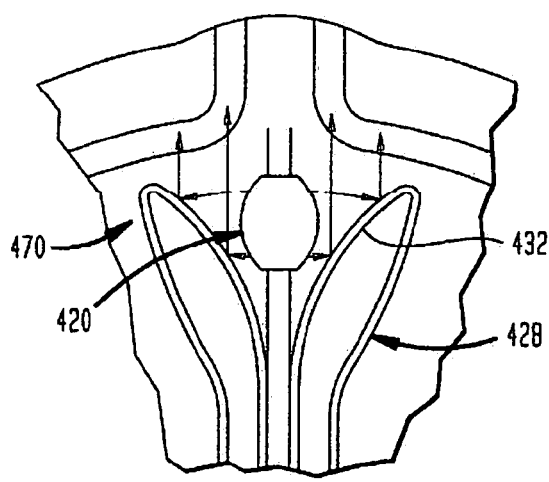

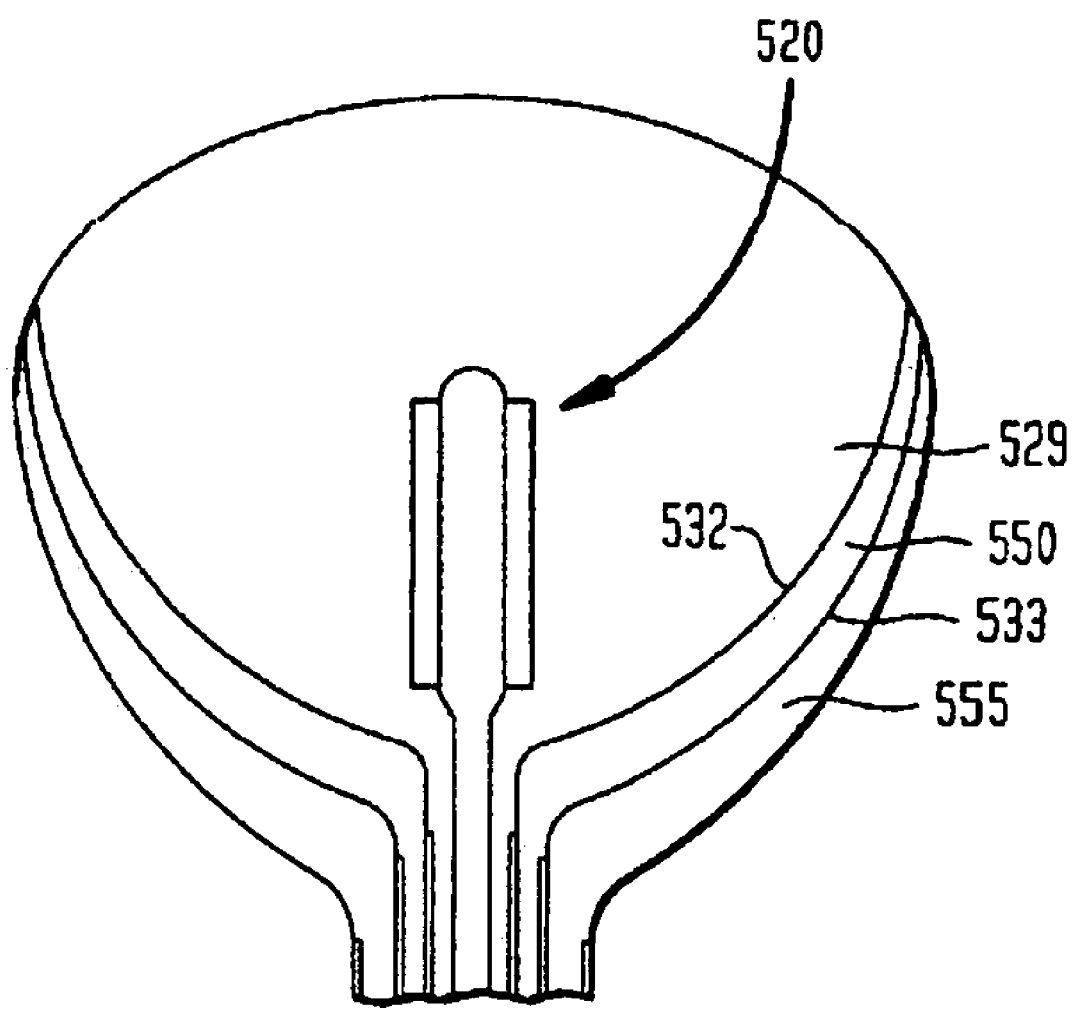

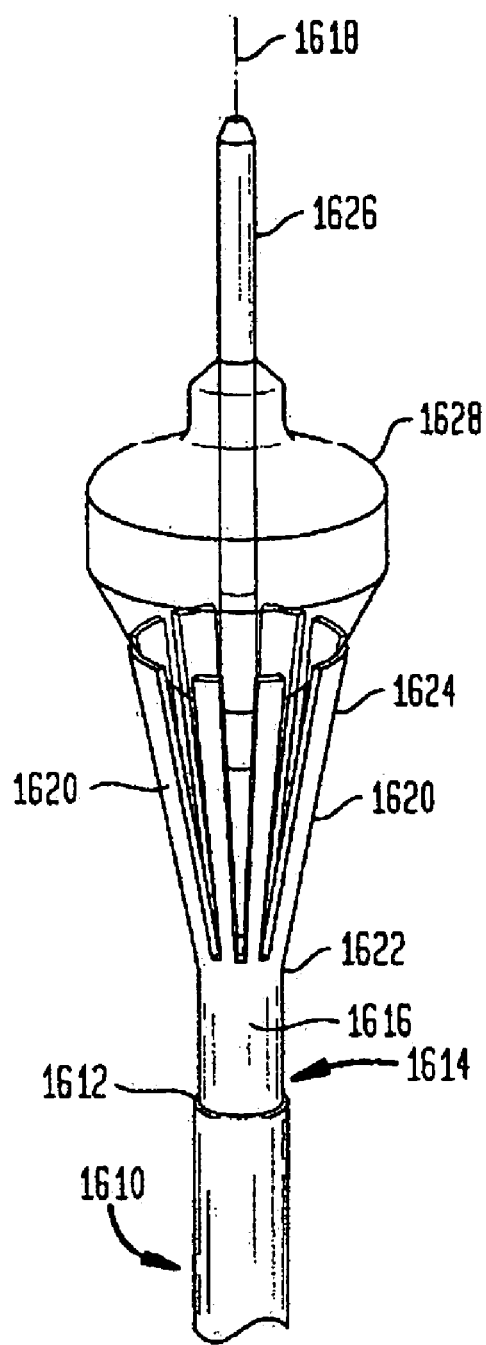
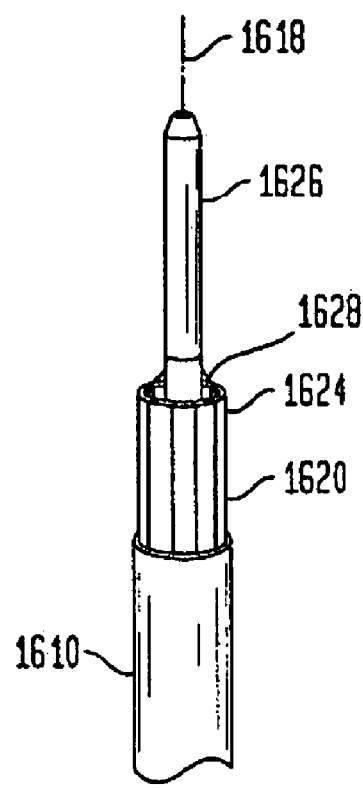

THERMAL TREATMENT METHODS AND APPARATUS WITH FOCUSED ENERGY APPLICATION

CROSS-REFERENCE TO RELATED APPLICATIONS

The present application is a continuation of U.S. patent application Ser. No. 10/227,092, filed Aug. 23, 2002 now U.S. Pat. No. 7,083,614, which application is a divisional of U.S. patent application Ser. No. 09/905,227, filed Jul. 13, 2001, now U.S. Pat. No. 6,635,054, which claims benefit of the filing date of U.S. Provisional Patent Application Ser. No. 60/218,641, filed Jul. 13, 2000, the disclosures of which are incorporated by reference herein.

FIELD OF THE INVENTION

The present invention relates to medical procedures such as cardiac ablation and to devices and components useful in these and other uses.

BACKGROUND OF THE INVENTION

Contraction or "beating" of the heart is controlled by electrical impulses generated at nodes within the heart and transmitted along conductive pathways extending within the wall of the heart. Certain diseases of the heart known as cardiac arrhythmias involve abnormal generation or conduction of the electrical impulses. One such arrhythmia is atrial fibrillation or "AF." Certain cardiac arrhythmias can be treated by deliberately damaging the tissue of the cardiac wall along a path crossing a route of abnormal conduction. This causes formation of a scar extending along the path where disruption occurred. The scar blocks conduction of the electrical impulses. Such a scar can be created by conventional surgery, but this entails all of the risks and expense associated with cardiac surgery. Another approach, described in Swartz et al., U.S. Pat. No. 5,575,766, is to introduce a catheter bearing a localized energy emitter such as an electrode for application of radio frequency ("RF") energy at its distal tip into a heart chamber, such as the right or left atrium of the heart in the case of atrial fibrillation. The physician then moves the catheter so that the tip, and the localized emitter traces the desired path. In AF, the desired path typically is a closed loop encircling the openings or ostia of the pulmonary veins. RF energy applied through the electrode heats the tissue to a degree sufficient to cause death of the normal tissue and its replacement by scar tissue. Heating to this degree is referred to herein as "ablation." Typically, heating to about 60-80° C. is sufficient. Tracing a precise path along the interior of a chamber in the heart of a living subject with the tip of a catheter involves inherent practical difficulties. Although curved guide wires can be placed within the catheter so that the catheter tip will tend to follow the guide wire as the physician moves it, the process is still difficult.

Swanson et al., U.S. Pat. No. 5,582,609 describes an elongated catheter having numerous RF electrodes disposed along its length in a distal region adjacent the tip. This distal region can be formed into a curved, loop-like configuration and manipulated so that the electrodes lie along the desired path, whereupon RF energy is applied so as to ablate cardiac tissue. In a variant of this approach, the electrodes are mounted on a structure which opens to form a ring-like configuration. Even with these structures, however, it is difficult to assure the desired placement of the RF electrodes.

Lesh, U.S. Pat. No. 5,971,983 describes an elongated catheter which is equipped with similar RF electrodes distributed over its distal region, and uses guide wires to position the distal region in place against the wall of the heart. Although this patent mentions an "ultrasonic element such as an ultrasound crystal element" along with numerous other devices as theoretically applicable to cardiac tissue ablation, it offers no structure for an elongated ultrasonic ablating device.

As described in Lesh, International Publication WO 99/02096, the abnormal conduction routes in AF typically extend from the wall of the heart along the pulmonary veins. Therefore, AF can be treated by ablating tissue in a ring around each pulmonary vein at the juncture between the pulmonary vein and the heart. As described in the '096 publication, such ablation can be performed by threading a catheter having a thermal ablation element at its distal tip into the heart so that the tip is lodged within the appropriate pulmonary vein. The catheter may bear a balloon which is inflated within the vein and which holds the catheter in place. The ablating element is then actuated so as to apply heat in a region surrounding the ablating element. In certain embodiments taught in the '096 publication, the ablating element includes a radio frequency ("RF") emitting element which is carried on the surface of the balloon. Ablation of the pulmonary vein using RF energy can create a rough, disrupted surface on the interior of the vein. This or other factors can lead to stenosis of the pulmonary vein or thrombosis, i.e., formation of blood clots.

Other embodiments described in the '096 publication disclose the use of ultrasonic transducers. The preferred ultrasonic transducer illustrated in the '096 publication is a rigid ceramic piezoelectric element disposed on a catheter surrounded by a balloon. When the balloon is inflated, the piezoelectric element remains remote from the wall of the pulmonary vein. The piezoelectric element can be actuated to apply sonic energy through a fluid contained in the balloon, thereby heating the ring of vein wall tissue surrounding the balloon. As a further alternative, the '096 publication shows an ultrasonic emitter in the form of a hollow concave disk. The '096 publication suggests that such an emitter can be physically rotated around the axis of a catheter so as to ablate a ring-like zone. These transducers have numerous drawbacks even for use in ablation of a vein wall and are not adapted for ablation of the wall of the cardiac chamber.

Ultrasonic heating such as high intensity focused ultrasound (HIFU) is utilized for certain therapeutic applications. As disclosed in commonly assigned International Application PCT/US98/1062, published as International Publication WO/98/52465 the disclosure which is hereby incorporated by reference herein, HIFU heating typically is conducted using an ultrasonic emitter having an array of transducers. The transducers are actuated with a drive signal so as to emit ultrasonic waves. The relative phasing of the waves is controlled by the physical configuration of the array and the phasing of the drive signal. These factors are selected so that the ultrasonic waves tend to reinforce one another constructively at a focal location. Tissue at the focal location is heated to a greater extent than tissue at other locations. As described, for example in U.S. Pat. Nos. 6,461,314 and 6,492,762, the disclosures of which are also incorporated by reference herein, HIFU may be applied by transducer arrays such as arrays of polymeric piezoelectric transducers. These arrays can be mounted on a probe such as a catheter which can be introduced into the body as, for example, within the vascular system or into a cavernous internal organ. The '314 patent discloses certain transducer arrays which can be deformed so as to vary the placement of the focal location.

Despite all of these efforts in the art, there have been needs for further improvements in the devices and methods used to apply thermal energy to the cardiac wall for treatment of atrial fibrillation, particularly the need to tightly control the zone of damage to cardiac tissue in order to minimize collateral damage to neighboring tissues. There have been corresponding needs for further improvement in the devices and methods used to apply energy to other organs of the body for thermal treatment.

SUMMARY OF THE INVENTION

The present invention addresses these needs.

One aspect of the present invention provides apparatus for applying energy within the body of a living subject. Apparatus according to this aspect of the invention preferably includes a probe having a proximal end and a distal end adapted for insertion into the body of the patient. For example, the probe may include one or more catheters. An ultrasonic emitter is provided adjacent the distal end of the probe.

The apparatus according to this aspect of the invention also includes an expansible structure mounted on said probe adjacent the distal end thereof. The expansible structure has a collapsed condition and an expanded condition. The expansible structure includes a reflector balloon having an interior space. The ultrasonic emitter is disposed outside of the interior space of the reflector balloon. The reflector balloon has an active region juxtaposed with the emitter when the expansible structure is in the expanded condition, so that ultrasonic energy emitted by the emitter will impinge on the active region from outside of the reflector balloon. Thus, when the reflector balloon is inflated with a gas and a liquid is present outside of the reflector balloon, the gas within the reflector balloon and the liquid will form a reflective interface at the active region. Ultrasonic energy emitted by the emitter will be reflected from the active region towards tissue of the subject adjacent the expansible structure.

Most preferably, the expansible structure further includes a structural balloon having an interior space encompassing the ultrasonic emitter. The structural balloon and the reflector balloon preferably are contiguous in the active region. Most preferably, the two balloons share a common wall at the active region. In operation, the structural balloon may be inflated with a liquid, so that the reflective interface is formed at the common wall by the liquid in the structural balloon and the gas in the reflector balloon. For example, the probe may have separate conduits communicating with the interior spaces of the two balloons.

The structural balloon desirably has a transmissive wall adapted to overlie a wall of an internal organ of the subject when said expansible structure is in said expanded condition. In this condition, the active region is configured so that ultrasonic energy will be reflected from the active region, through the interior space of the structural balloon to the transmissive wall. The ultrasonic energy will pass through the transmissive wall to the wall of the internal organ. The liquid in the structural balloon desirably is an aqueous liquid or other liquid having acoustic impedance close to that of the body tissue to minimize reflection at the interface with the tissue.

Most preferably, the ultrasonic emitter is substantially in the form of a surface of revolution about a central axis extending in forward and rearward directions, and the active region is also substantially in the form of a surface of revolution about the central axis when the expansible structure is in its expanded condition. Thus, the active region can direct energy into an annular treatment region in the form of an annular or loop-like path extending along the wall of the organ around the central axis.

Most preferably, the active region is adapted to focus the ultrasonic energy reflected at the active region into a loop-like focal region which extends along the path but which has area smaller than the active region. In this manner, the ultrasonic energy is concentrated to provide a high energy density, so that the applied ultrasonic energy provides rapid heating along the entire path. For example, the active region may be a surface of revolution of a parabola about the central axis. As further explained below, such a surface will focus energy from a simple cylindrical ultrasonic emitter into an annular focal region.

Preferred apparatus according to this aspect of the invention can be used, for example, to ablate tissue of the wall of the atrium encircling the ostium of a pulmonary vein. Tissue along an annular path of about 25-30 mm diameter can be ablated so as to form a full transmural lesion, extending entirely through the atrial wall to provide a full conduction block, in a few minutes or less, using about 15 Watts of ultrasonic power. Even shorter ablation times can be achieved using higher power.

The ability to treat tissue along an annular path of large diameter is particularly advantageous inasmuch as it allows formation of the lesion in the cardiac wall, rather than in the pulmonary vein itself. This minimizes stenosis of the pulmonary vein, which is a significant drawback of pulmonary vein ablation. However, the expansible structure and transducer can be extremely compact when in the collapsed condition. Preferably, the expansible structure and transducer are about 4 mm or less in diameter when in the collapsed condition, and can be placed into the heart by threading the probe through the vascular system.

The apparatus desirably is arranged to place the focal region within the wall of the organ, at a desired depth from the surface of the wall. Ultrasonic ablation using a focal region within the wall minimizes formation of rough scar tissue at the wall surface, and thus minimizes thrombogenesis when the apparatus is used to treat the heart. Placement of the focal region within the wall also promotes rapid heating.

Preferably, the structural balloon has properties similar to those of a balloon regarded as a "noncompliant" balloon in the arts of balloon angioplasty and related arts. Such a balloon is quite rigid when inflated, and is not deformed appreciably by physiologic pressures such as the pressure of blood. Typically, such balloons are inflated to significant pressure, typically several atmospheres or more. In the preferred embodiments, the structural balloon maintains the active region in a precise shape to assure sharp focusing, and helps to position the expansible structure with respect to the heart or other organ to be treated so as to provide precise placement of the focal region.

A related aspect of the invention provides apparatus for applying energy within a subject. The apparatus according to this aspect of the invention provides an expansible structure for insertion into the body of the subject. The expansible structure includes a reflector having an active region. The expansible structure has a collapsed condition and an expanded condition. The apparatus also includes an energy emitter operative to apply energy while the expansible structure is in the expanded condition and disposed within the body of the subject so that the applied energy is directed onto the active region of the reflector and reflected by the active region of the reflector towards the tissue of the subject adjacent the reflector. Most preferably, the expansible structure is operative to focus the energy as well as redirect it. The focusing action preferably is provided by the active region of the reflector, although, as explained below, other expansible elements such as an inflatable lens can be used to provide focusing. The ability to provide both focusing and reflective redirection in the expansible structure contributes to the action of the apparatus as discussed above. In this aspect of the invention, the energy emitter most preferably is an ultrasonic emitter, although other forms of energy may be applied.

A related aspect of the invention provides methods of applying energy to a living subject including the steps of positioning an expansible structure including a reflector, such as the structures discussed above with reference to the apparatus, within or adjacent to the body of the subject and bringing the expansible structure to an expanded condition. The method further includes the step of directing energy onto an active region of the reflector so that energy is reflected from the active region and directed onto a desired region of the subject. Most preferably, the expansible structure focuses the energy in addition to redirecting it. The expansible structure may be disposed within the body of the subject in or adjacent to an organ and the energy may be directed onto a desired region of the wall of the organ as, for example, onto the interior wall of a heart chamber. As discussed above in connection with the apparatus, the energy may be sonic energy such as ultrasonic waves. In one particularly preferred method, the expansible structure is positioned within a chamber of the heart and the energy is directed onto a treatment region extending along an elongated path on the interior wall of the heart as, for example, along a path at least partially surrounding and desirably entirely surrounding the ostium of a blood vessel communicating with the heart chamber, such as the ostium of a pulmonary vein. Desirably, energy is directed onto the entire path simultaneously. Because the entire path can be ablated or otherwise treated simultaneously, there is no need to reposition the probe carrying the expansible structure during the procedure.

The preferred apparatus and methods according to the foregoing aspects of the invention are simple and inherently reliable. Merely by way of example, the most preferred apparatus can employ simple ultrasonic transducers with a single piezoelectric element, and balloon structures which can be fabricated with known techniques.

A further aspect of the present invention provides an acoustic reflector for directing ultrasonic energy comprising a first or structural balloon and a second or reflector balloon, the balloons being inflatable and deflatable. The balloons are contiguous with one another at an active region at least when the balloons are in an inflated condition. The structure desirably includes a first port communicating with the interior of the first balloon and a second port communicating with the interior of the second balloon, so that the first and second balloons can be filled with different fluids having different acoustic impedances so as to form a reflective interface at the active region. A structure in accordance with this aspect of the invention can be used as a component of the apparatus described above, or in other applications.

Another aspect of the invention provides techniques of monitoring and controlling cardiac ablation procedures as discussed above. Still other aspects of the invention provide features which facilitate orderly collapse of the balloon structures after use, so as to facilitate withdrawal of the apparatus after the procedure.

These and other objects, features and advantages of the present invention will be more readily apparent from the detailed description of the preferred embodiments set forth below, taken in conjunction with the accompanying drawings.

BRIEF DESCRIPTION OF THE DRAWINGS

FIGS. 5, 6, 7 and 8 are fragmentary diagrammatic views depicting apparatus according to further embodiments of the invention.

FIGS. 17 and 18 are fragmentary perspective views depicting apparatus according to yet another embodiment of the invention during different phases of operation.

DETAILED DESCRIPTION OF THE PREFERRED EMBODIMENTS

Figure 1:
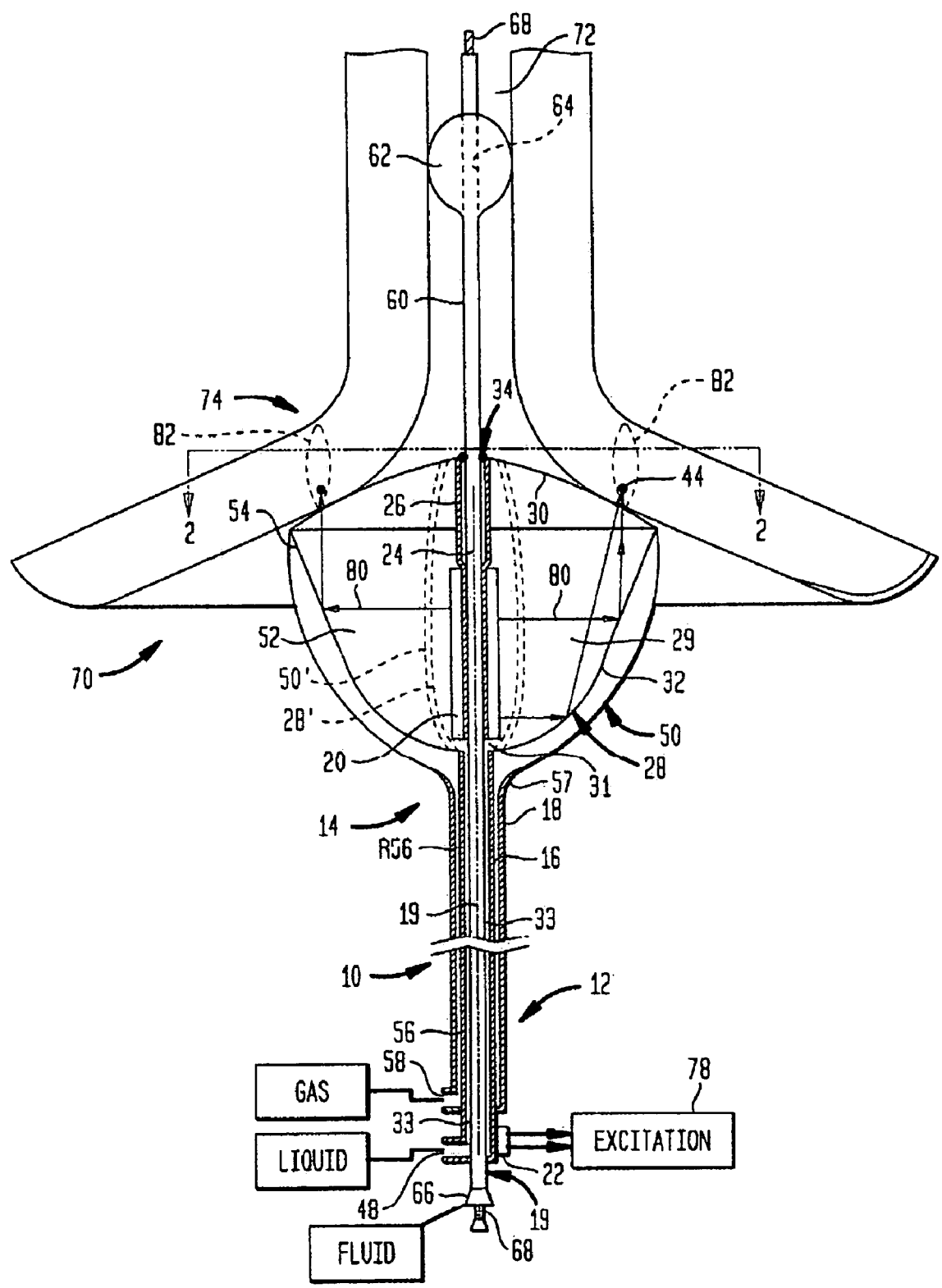
FIG. 1 is a diagrammatic view of apparatus in accordance with one embodiment of the invention in conjunction with a portion of a heart and pulmonary vein.

Apparatus according to one embodiment of the invention includes a probe structure 10 having a proximal end 12 and a distal end 14. A portion of the probe structure between the proximal and distal ends is omitted in FIG. 1 for clarity of illustration. The probe structure includes a tubular first catheter 16, a tubular second catheter 18 surrounding the first catheter and a tubular guide catheter 19 extending within the first catheter. The first catheter 16 carries a cylindrical ultrasonic transducer 20 adjacent its distal end. The cylindrical ultrasonic transducer may be a ceramic piezoelectric element such as lead titanate or a polymeric piezoelectric transducer such as PVDF-TRF (polyvinylidene fluoride-trifluoroethylene) copolymer transducer. A ceramic piezoelectric transducer typically is formed as a single hollow cylinder of ceramic piezoelectric material with thin metallic electrodes (not shown) disposed on its interior and exterior surfaces. A cylindrical polymeric piezoelectric transducer may include one or more layers of polymeric piezoelectric material with electrodes between each pair of adjacent layers and further electrodes on the interior and exterior surfaces. A polymeric piezoelectric transducer typically is provided with a rigid backing on its interior surface as, for example, a metallic or ceramic tube (not shown). The electrodes of transducer 20 are connected to electrical conductors (not shown) extending within or along first catheter 16 to a connector 22 at the proximal end of the first catheter.

The first catheter and the cylindrical transducer 20 define a central axis 24 adjacent the distal end of the probe structure. The first catheter has a distal tip 26 projecting distally beyond the transducer 20. A first balloon 28, also referred to herein as a "structural balloon," is mounted to the first catheter at the distal end thereof. The first balloon includes an active wall 32 formed from film which is flexible but which can form a substantially noncompliant balloon structure when inflated. Materials similar to those used to form noncompliant balloons in the angioplasty art, such as films of PET, PETG, nylon, polyurethane, polyethylene and other polymers can be used. Typically, such balloons are inflated to a relatively high preselected inflation pressure, referred to herein as the "design inflation pressure", such as a few atmospheres to 10 or 12 atmospheres. Inflation pressures of this order render the balloon relatively rigid. Stated another way, the balloon will assume a predictable, preselected shape when inflated to the design inflation pressure, with minimal deviation from this shape despite variations in external pressure applied by the surrounding blood and soft tissue. The balloon wall desirably has the minimum thickness required to withstand the design inflation pressure without rupturing, as, for example, about 0.001 inches (1 mil) or less, preferably about 0.5 mils or less. In the inflated condition of the balloon depicted in FIG. 1, wall 32 is in the form of a surface of revolution about a central axis 24. The largest diameter of the balloon desirably is about 24-28 mm. The forward wall 30 may be formed from the same materials as wall 32 or from a different material. Preferably, however, the entire balloon is formed as an integral unit from a single material, as by blow-molding a tube or parison of PET or other polymer. The forward wall 30 is generally annular and has a central opening 34 surrounding central axis 24. The forward wall 30 may be generally conical or dome-shaped and may project forwardly from its juncture with active wall 32. For example, the forward wall 30 may be conical, with an included angle of about 120 degrees. The forward wall 30 joins the wall of first catheter 16 at the distal tip 26 thereof, whereas the active wall 32 joins the wall of the catheter 16 proximally of the transducer 20. Thus, the transducer 20 is disposed inside of first balloon 28.

Figure 3:
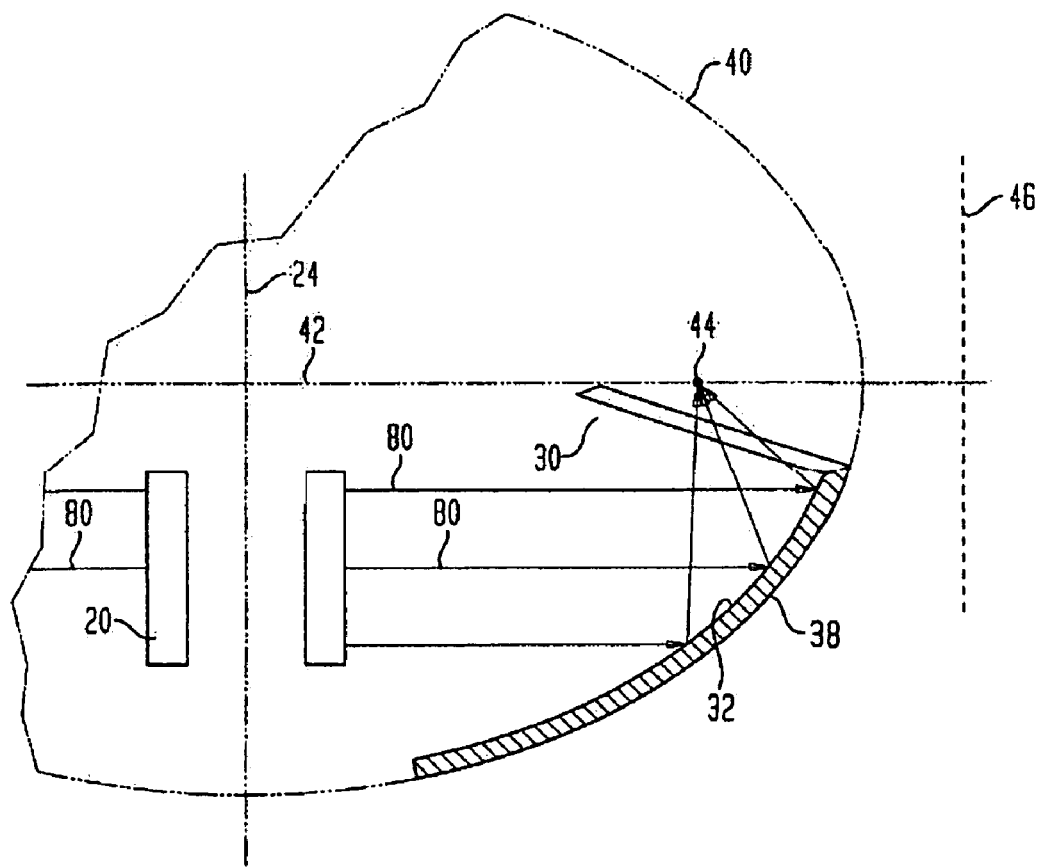
FIG. 3 is a fragmentary diagrammatic view depicting certain geometrical relationships in the apparatus of FIG. 1.

The shape of active wall region 32 depicted in FIG. 1 may be that of a surface of revolution about central axis 24 formed by rotation of a generatrix or curve 38 (FIG. 3) which is a portion of a parabola 40 having its principal axis 42 transverse to and desirably perpendicular to central axis 24. The principal axis 42 of the parabola is a line through the focus 44 of the parabola perpendicular to a line 46 referred to as the directrix of the parabola. By definition, the parabola is curved such that the distance of any point on the curve to focus 44 is equal to the distance from such point to directrix 46. Preferably, the forward wall 30 lies just to the rear or proximal side of focus 44. Stated another way, the focus 44 of the parabolic generatrix is slightly forward or distal of the forward wall 30 when the balloon is in the inflated condition. Although only one section of generatrix 38 and active region 32 is shown in FIG. 3, it should be appreciated that the focus is disposed in substantially the same location at all positions around central axis 24. Stated another way, the focus 44 of the surface of revolution is a circle surrounding central axis 24 just forwardly of the forward wall 30.

A port 31 connects the interior space 29 within the first or structural balloon 28 with the lumen or interior bore 33 of the tubular first catheter 16. The first catheter has a fitting 48 at its proximal end communicating with this lumen so that a fluid may be introduced into the interior space 29 to inflate the first balloon 28 or withdrawn from the first balloon to deflate it. In the deflated condition depicted in broken lines in FIG. 1, when the first balloon is in the deflated condition depicted in broken lines at 28', the first balloon is collapsed radially inwardly and closely overlies the exterior of first catheter 16 and transducer 20.

A second balloon 50, also referred to herein as the "reflector balloon," is carried on the distal end of second catheter 18. Balloon 50 has a partial wall partially enclosing the interior space 52 within the second balloon. The partial wall is disposed slightly to the rear or proximally of the active wall region 32 of the first balloon, so that the partial wall of balloon 50 overlies the active wall region 32 of the first or structural balloon. The wall of balloon 50 joins the wall of balloon 28 at a juncture 54 near the forward edge of the active wall region 32. Thus, the interior space 52 within the second balloon 50 is partially bounded by the wall of balloon 50 and partially bounded by the active wall region 32 of balloon 28. The active wall region 32 is a common wall forming portions of both the first and second balloons and separating the interior space 29 of the first balloon from the interior space 52 of the second balloon. The interior space 52 of the second balloon communicates with the lumen 56 within second catheter 18 at a port 57 defined by the distal end of the second catheter and surrounding the first catheter 16. The second catheter has a fitting 58 at its proximal end, so that a fluid can be introduced into the interior space 52 of the second balloon through port 58, lumen 56 and port 57 to inflate the second balloon and the fluid can be withdrawn to deflate the second balloon. When both the first and second balloons are in the deflated position, the second balloon is also collapsed inwardly, toward the central axis 24 so that the second balloon in the deflated condition 50' closely overlies the deflated first balloon 28'. The partial wall of balloon 50 may be formed from a material such as a urethane, as, for example, by thermoforming, and may be bonded to the wall of balloon 28 by an adhesive at the forward edge of the partial wall.

The guide catheter 19 extends within the interior lumen 33 of first catheter 16 and extends through the distal tip 26 of the first catheter so that a distal tip 60 of the guide catheter projects through the central opening 34 of the forward wall 30 of the first balloon. Guide catheter 19 is also hollow and has two lumens (not shown). An expansible anchor balloon 62 surrounds the outside of distal tip 60 and communications with one lumen of the guide catheter through a port 64. The guide catheter is provided with a fitting 66 communicating with this lumen at its proximal end so that the guide catheter and anchor balloon 62 can be connected to a source of fluid for inflation and deflation. The other lumen of the guide catheter is arranged to pass a guide wire 68.

In a method according to one embodiment of the invention, guide wire 68 is threaded through the circulatory system of a living subject such as a human or other mammalian subject suffering from atrial fibrillation and into the interior space 70 within the left atrium of the subject's heart. The guide wire is further threaded into a pulmonary vein 72. The proximal end of the guide wire, outside of the patient's body, is disposed in a lumen of guide catheter 19. Once the guide wire has been placed within the pulmonary vein, the probe structure, with first balloon 28, second balloon 50 and anchor balloon 62 deflated, is advanced along the guide wire and hence threaded through the subject's circulatory system until anchor balloon 62 is disposed within the pulmonary vein. Anchor balloon 62 is inflated with any suitable fluid such as saline solution to expand the anchor balloon and anchor it in a place within the pulmonary vein. This anchors the first and second balloons within the heart chamber 70. The forward wall 30 of the first balloon bears on the interior surface of the heart wall at the ostium or opening 74 at which pulmonary vein 72 communicates with heart chamber 70.

The first balloon 28 is inflated with water, saline solution or other aqueous fluid having acoustic impedance close to the acoustic impedance of body tissues. The second balloon 50 is inflated by filling its interior space 52 with a relatively small amount of gas such as carbon dioxide. The pressure within the interior space 29 of the first balloon is adjusted to the design inflation pressure of the first balloon. This pressure is substantially above the prevailing pressures within the heart and assures that the first balloon, and particularly active surface 32, is in its preselected configuration. The pressure within the second balloon is selected to be less than the pressure within the first balloon but still above the prevailing pressures within the heart. Any appropriate sources of liquid and gas can be used to inflate the first balloon. For example, a controlled-pressure source incorporating any convenient type of pressure regulator may be employed. The pressure within the interior space 52 of the second balloon is not critical; any gas pressure sufficient to push the wall of balloon 50 away from the active wall region 32 of the first balloon, but not so great as to rupture the second balloon may be employed.

The aqueous liquid within the interior space 29 of the first balloon and the gas within the interior space 52 of the second balloon form a reflective interface at the active wall region 32, i.e., at the common wall separating the interiors of the first and second balloons. Thus, although the material of the active wall region 32 itself forms part of the interface, the reflectivity of the interface is determined mainly by the acoustic impedances of the fluids on opposite sides of the wall. The reflectivity of the interface is given by the formula:

$$R=(Z_{29}-Z_{52})/(Z_{29}+Z_{52})$$

where:

R is the reflectivity of the interface;

$Z_{29}$ is the acoustic impedance of the fluid within the interior space 29 of the first balloon 28; and $Z_{52}$ is the acoustic impedance of the fluid in the interior space 52 of second balloon 50.

Acoustic impedance is sometimes described as the acoustic velocity or speed of sound in a medium multiplied by the density of the medium. More accurately, acoustic impedance is defined as the acoustic pressure divided by the volume velocity. Volume velocity is the velocity that the particles in the medium are moving. Typical aqueous fluids have acoustic impedance of about 1.5 MRayls, whereas typical gases have acoustic impedance of less than about $10^{-4}$ MRayls, so that the reflectivity at the active region or interface 32 typically is at least about 0.9 and more typically nearly 1.0.

Figure 2:
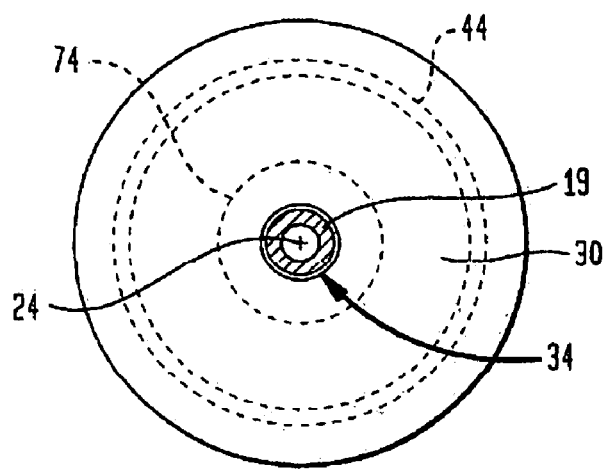
FIG. 2 is a diagrammatic sectional view taken along line 2-2 in FIG. 1.

Transducer 20 is connected to a source 78 of electrical excitation signals through connector 22 and the transducer is actuated to produce ultrasonic waves. The ultrasonic waves propagate substantially radially outwardly as indicated by arrows 80 in FIGS. 1 and 3. Stated another way, the cylindrical transducer produces substantially cylindrical wave fronts which propagate generally radially outwardly. These waves are reflected by the interface at active region 32. Because the interface has a parabolic shape, the waves striking any region of the interface will be reflected substantially to the focus 44 defined by the surface of revolution, i.e., into a substantially annular or ring-like focal region at focus 44. As best seen in FIG. 2, this ring-like focus surrounds the central axis 24 and surrounds the ostium 74 of the pulmonary vein. This focal region is slightly forward of the forward wall 30 and hence within the heart tissue, near the surface of the heart wall. For example, the focal region may be disposed at a depth equal to about one-half of the thickness of the heart wall as, for example, about 2-4 mm from the surface of the wall. Because the fluid within the interior of balloon 29 has an acoustic impedance close to that of the heart tissue itself, there is a minimal reflection at the interface between the forward wall 30 of the first balloon and the heart wall; substantially all of the ultrasonic energy reflected from the active region 32 passes into the heart wall and to the focal region 44. Also, the total distance traveled by the acoustic waver, radially outwardly from the cylindrical surface of transducer 20 to the active region 32 and from the active region to the focus 44 is the same for any waves emanating from any axial position along the length of transducer 20. Therefore, the ultrasonic energy from various portions of the cylindrical transducer will constructively reinforce ultrasonic energy from other portions of the transducer. That is, the wave front from various portions of the transducer will arrive at the focal region substantially in phase with one another. Therefore, the heart wall tissue within focal region 44 will be heated rapidly. The rapid heating effectively ablates or kills the tissue within the focal region so that a wall of non-conductive scar tissue forms in the focal region and in neighboring tissue. Some of the ultrasonic energy is absorbed between the surface of the wall and the focal region, and at locations deeper within the wall than the focal region. To provide a complete conduction block, tissue should be ablated through the entire thickness of the wall, so as to form a transmural lesion. With a transducer capable of emitting about 15 Watts of acoustic energy, an ablated region extending entirely through the heart wall can be formed within a few minutes of actuation. Higher power levels as, for example, above 30 Watts of acoustic energy and desirably about 45 Watts are preferred because such power levels will provide shorter lesion formation time. Because the sonic energy is directed simultaneously into the entire loop-like path surrounding the pulmonary vein, the entire procedure can be performed without repositioning the probe.

Ultrasonic heating and ablation offer numerous advantages over conventional RF heating. In particular, there is little or no tendency for rough scar tissue to form on the wall surface of the heart. This is particularly important inasmuch as rough scar tissue formed by conventional RF heating procedures tends to provoke thrombosis or formation of blood clots. These clots can occlude the pulmonary vein or can travel in the circulatory system and occlude other blood vessels with serious consequences. Moreover, ablation around the ostium, to place the ablated region in the atrial wall, rather than inside the pulmonary vein, avoids damage to the delicate structure of the pulmonary vein and thus entirely avoids or minimizes stenosis of the pulmonary vein. For treatment of a normal adult human, the focal region desirably has a diameter of about 25-30 mm.

After the ablation procedure has been performed, the various balloons are deflated and the entire apparatus is withdrawn.

Apparatus according to a further embodiment of the invention includes a probe structure incorporating a first catheter 116 and a second catheter 118, together with a first balloon 128 and second balloon 150 similar to the corresponding elements discussed above with reference to FIGS. 1-3. However, the active region 132 in its inflated condition does not have a parabolic configuration. Instead, the active surface is substantially conical and concentric with the central axis 124 of the sonic transducer 120 and probe structure 110. Thus, within the active region, the common wall 132 between the interior space 129 of the first balloon and the interior space 152 of the second balloon slopes forwardly at a substantially constant angle to the central axis. Sonic transducer 120 is carried on an additional catheter 101 slidably mounted within the first catheter 116. The additional catheter has a central bore 102 and an auxiliary bore 103. A guide catheter 160 is received within the central bore 102 of the additional catheter. The guide catheter is sealed to the forward wall 130 of the first balloon. An additional balloon 104 surrounds the cylindrical sonic transducer 120. The additional balloon 104 is formed from a flexible material such as those discussed above with reference to the active region of the first balloon. Thus, balloon 104 has a predictable, preselected shape when inflated. Balloon 104, in a fully inflated condition, has a shape of surface of revolution about central axis 124. The generatrix of the surface of revolution is convex so that it is at a maximum distance from the central axis at a point adjacent the axial medial plane 105 of the sonic transducer and curves radially inwardly, toward central axis 124 from this axial medial plane. Because this balloon will serve as an acoustic lens during operation of the device, balloon 104 is also referred to herein as the "lens balloon." Lens balloon 104 communicates with the auxiliary bore 103 of additional catheter 101. The additional catheter 101, transducer 120 and lens balloon 104 are slidable in the axial or proximal and distal directions relative to the first catheter 116, guide catheter 160 and first balloon 128.

In use, the apparatus is placed in substantially the same way as discussed above. Once the balloons are disposed within the heart chamber, the first and second catheters are inflated by placing a liquid into the interior space 129 of the first balloon through the lumen of first catheter 116 and by introducing a gas through the lumen of second catheter 118 into the interior space 152 of the second balloon in substantially the same way as discussed above. Lens balloon 104 is inflated through additional lumen 103 of catheter 101 with a fluid having an acoustic velocity less than that of the aqueous liquid within interior space 129 of the first balloon but having an acoustic impedance close to that of the liquid in space 129. For example, fluorocarbon liquids sold under the registered trademark FLUORINERT have acoustic velocity less than that of water but have acoustic impedance close to that of water.

Figure 4:
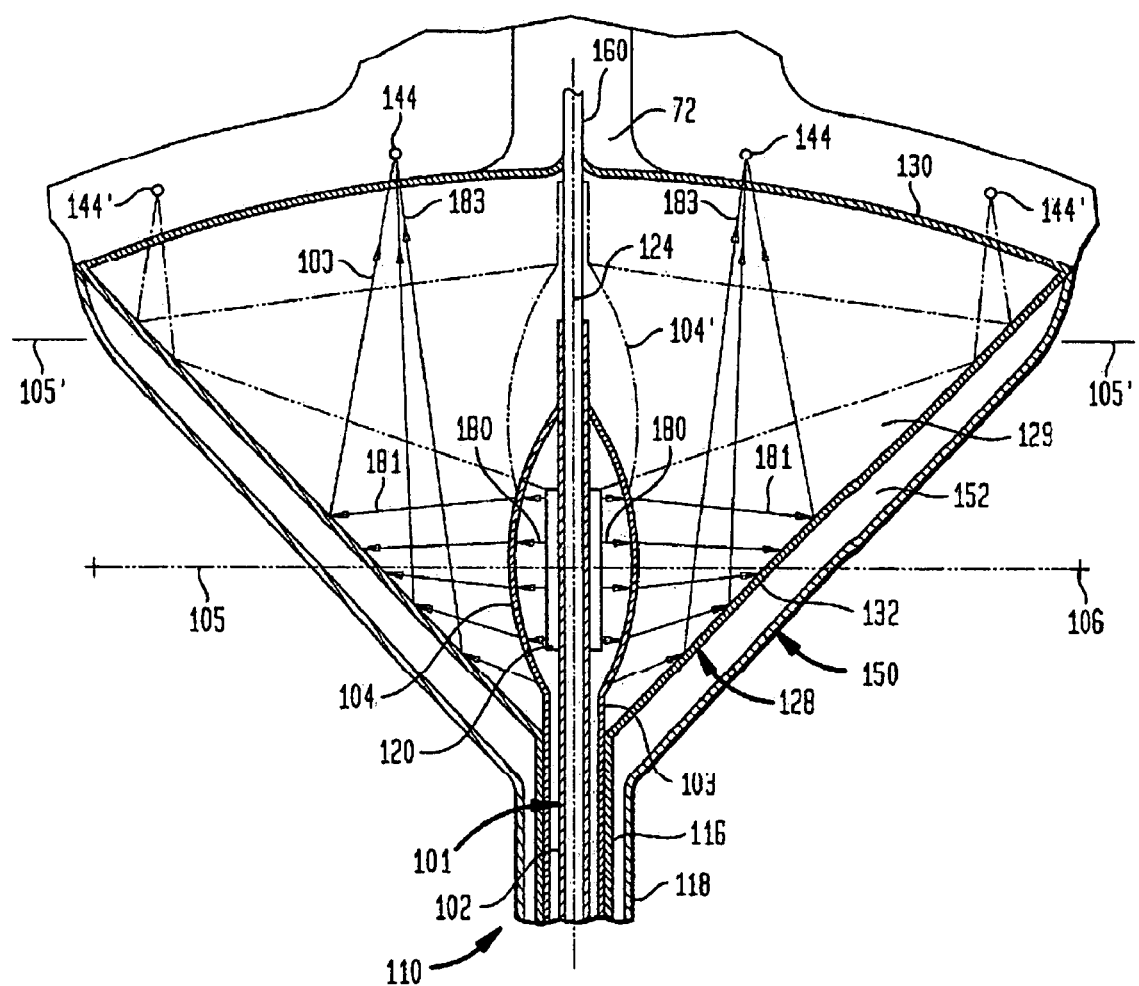
FIG. 4 is a view similar to FIG. 1, but depicting apparatus according to a further embodiment of the invention.

With the acoustic emitter 120 and lens balloon 104 in the position indicated in solid lines in FIG. 4, the acoustic emitter is actuated as discussed above. Here again, the acoustic emitter emits acoustic waves which propagate substantially radially within lens balloon 104 as indicated by arrows 180 in FIG. 4. As these waves encounter the interface between the fluid in lens balloon 104 and the fluid in the interior space 129 of the first balloon, they are refracted into a convergent pattern indicated by arrows 181. The convergent acoustic waves are focused towards an annular focus 106 on medial plan 105, concentric with the central axis 124. Because the acoustic impedances on the inside and outside of lens balloon 104 are well matched, there is only minimal reflection of ultrasonic waves at this interface.

As the convergent acoustic waves 181 pass outwardly towards focus 106, they encounter the interface at the active region 132 of the first balloon wall and are reflected generally axially as indicated by arrows 183 so that the acoustic waves converge and reinforce one another in a circular focal region 144 encircling the central axis 124 forward of the forward wall 130 of the first balloon. Thus, the apparatus applies thermal treatment to a portion of the tissue in the heart wall in the focal region 144 so as to ablate the tissue in and around the focal zone. Here again, the tissue is ablated along the substantially closed ring-like path encircling the ostium of pulmonary vein 72, and the thermal treatment is performed at substantially all points along the path simultaneously. After a desired thermal treatment has been applied along one focal region 144, the sonic emitter 120 and lens balloon 104 may be moved axially within the interior of first balloon 120 to the position indicated in broken lines at 104' and the sonic emitter may be actuated again. With the sonic emitter and lens balloon in position 104', the outwardly propagating ultrasonic waves are focused towards medial plane 105'. Accordingly, the ultrasonic waves intersect the active region 132 of the reflector at a relatively large radius from central axis 124, so that the reflected ultrasonic waves are focused at a different focal region 144'. Focal region 144' is a ring-like region encircling the central axis 124 at a larger radius than the original focal region 144. Thus, the tissue surrounding region 144' may be subjected to the thermal treatment. Once again, the tissue in a loop-like path encircling the ostium of the pulmonary vein is treated. The emitting element and lens balloon may be moved to positions between the position indicated in solid lines and the position indicated in broken lines so as to bring the ultrasonic waves into focus in a ring-like focal region having a radius larger than that of focal region 144 but smaller than that of focal region 144'. Any number of such intermediate positions can be used so as to apply thermal treatment over any number of different focal regions. In a variant of this approach, the lens balloon and sonic emitter are moved over a range of positions while the sonic emitter operates continuously, so as to spread the applied sonic energy over a range of focal regions.

In a further variant (FIG. 5) the combination of a cylindrical emitting element and a lens balloon is replaced by an emitting element 220 substantially in the form of a surface of revolution but having sloping emitting surfaces 221 and 222 tilted towards a common medial plane 205 transverse to the central axis 224 of the emitting element so that these emitting surfaces will emit ultrasonic waves converging towards the medial plane 205. Such a non-cylindrical emitting element may be formed as a unitary mass of a ceramic or other rigid piezoelectric material. Alternatively, as disclosed in commonly assigned U.S. Provisional Patent Application Ser. No. 60/160,546, filed Oct. 20, 1999, the disclosure of which is hereby incorporated by reference herein, such an emitting element may be formed from one or more strips of a flexible piezoelectric material. Such strips may be wound into a spiral so that in a contracted condition the strip lies close to the central axis 224. When expanded the spiral strip or strips form a body of revolution having emitting surfaces lying generally along a surface of revolution about the central axis 224. Such a spiral-shaped transducer may include plural strips of piezoelectric material having emitting surfaces tilted in different directions disposed on opposite sides of a medial plane 205. As also disclosed in said application Ser. No. 60/160,546, such a transducer may be expanded or contracted by a further balloon 201 disposed inside of the spiral-wound piezoelectric material.

In the embodiment discussed above with reference to FIGS. 1-3, the focusing function is performed entirely by the active region 32 of the reflector structure, so that the reflector structure both focuses and redirects the sonic energy. By contrast, in the apparatus discussed above with reference to FIGS. 4 and 5, the focusing function is performed entirely by the lens balloon or the ultrasonic emitter and the reflector structure serves principally to redirect the sonic energy without further focusing it. In a further variant (not shown) some focusing is provided by a shaped transducer or lens and the reflector structure further focuses the ultrasonic energy. In yet another variant, an emitting assembly 320 (FIG. 6) disposed adjacent the central axis 324, such as a cylindrical emitter and lens as discussed above with reference to FIG. 4 or a shaped emitter as discussed with reference to FIG. 5, provides ultrasonic waves converging towards a medial plane 305 transverse to the central axis. The active region 324 of the reflector structure is shaped so that the reflected ultrasonic waves will be directed substantially along cylindrical paths which do not further converge. Stated in another way, the reflector structure acts to collimate the reflected ultrasonic waves in a beam 383 having a shape of a hollow cylinder with a relatively small radial thickness. In this variant, the ultrasonic waves directed into the wall 370 of the heart are not focused by the reflector structure. However, because the focusing action of the lens or shaped transducer concentrates the ultrasonic waves on a small region of the reflector, the ultrasonic waves from the entire transducer are concentrated into a correspondingly small cross-sectional area of the axial beam 383, so that substantial ultrasonic power is concentrated within a narrow ring-like path over the pulmonary vein 372. In this arrangement, the ultrasonic power is spread more evenly through the thickness of the heart wall in the axial direction.

Apparatus according to yet another embodiment (FIG. 7) includes a reflector structure which incorporates only a single balloon 428. The balloon is inflated with a gas or other medium having acoustic impedance substantially different from the acoustic impedance of blood or other aqueous fluid found within the interior of the heart chamber 470. The emitting assembly 470 is disposed outside of the first balloon so that acoustic waves traveling from the emitting assembly pass through the blood or other aqueous fluid contained within chamber 470 to the active region 432 of the reflector structure. Due to the impedance mismatch between the blood or other aqueous fluid and the gas inside balloon 428, there will be highly reflective interface at the active region 432. In substantially the same way as discussed above, the ultrasonic energy is reflected forwardly from the active region. As in the embodiments discussed above, the reflected beam may be convergent towards a focal region or may be collimated in a beam having the shape of a hollow cylinder.

Apparatus according to a further embodiment of the invention includes three balloons defining three interior spaces 529, 550 and 555 so that there is a first interface 532 between the first and second balloons and a second interface 533 between the second and third balloons, behind the first interface. When the first balloon is inflated with a liquid such as an aqueous liquid and the second balloon is inflated with a gas or other medium having acoustic impedance different from that of the liquid, the ultrasonic waves from emitting assembly 520 will be reflected at the first interface 532. In this condition, the fluid in the interior space 555 of the third balloon does not play any appreciable role in operation of the reflector structure. In a different operating condition, the interior spaces 529 and 550 are filled with liquids having substantially similar acoustic impedances, whereas the interior space 555 of the third balloon is filled with a gas or other fluid having substantially different acoustic impedance from the fluids in the first and second interior spaces. In this condition, there will be little or no reflection at the first interface 532, whereas there will be substantial reflection at the second interface 533. Thus, either interface 532 or interface 533 may serve as the active region of the reflective structure. This approach can provide reflective structures of different configurations and in different relationship to the emitting assembly 520. Thus, the focus or direction of the acoustic energy may be varied during operation by changing the fluids used to inflate the second balloon, so as to direct the acoustic energy into different regions of the organ to be treated as for example, into a deeper or shallower focus in the wall of the heart. In a further variant (not shown) a structure such as discussed above with reference to FIG. 1, which provides a focus at a substantially fixed location relative to the reflector structure can be moved so as to bring the active region of the reflector structure towards or away from the wall of the heart and thereby vary the depth of focus within the heart wall. For example, the reflector structure may be slidable with respect to the anchor 62 and guide catheter 60. Successive ablations or other thermal treatments can be performed using these different focus depths. In a further variant, the configuration of the reflector structure may be arranged so that movement of the emitter structure relative to the reflector structure, such as the movement discussed above with reference to FIG. 4, varies the depth of focus instead of the radial location of the focal region, or varies both the radial location and depth of the focal region.

Figure 9:
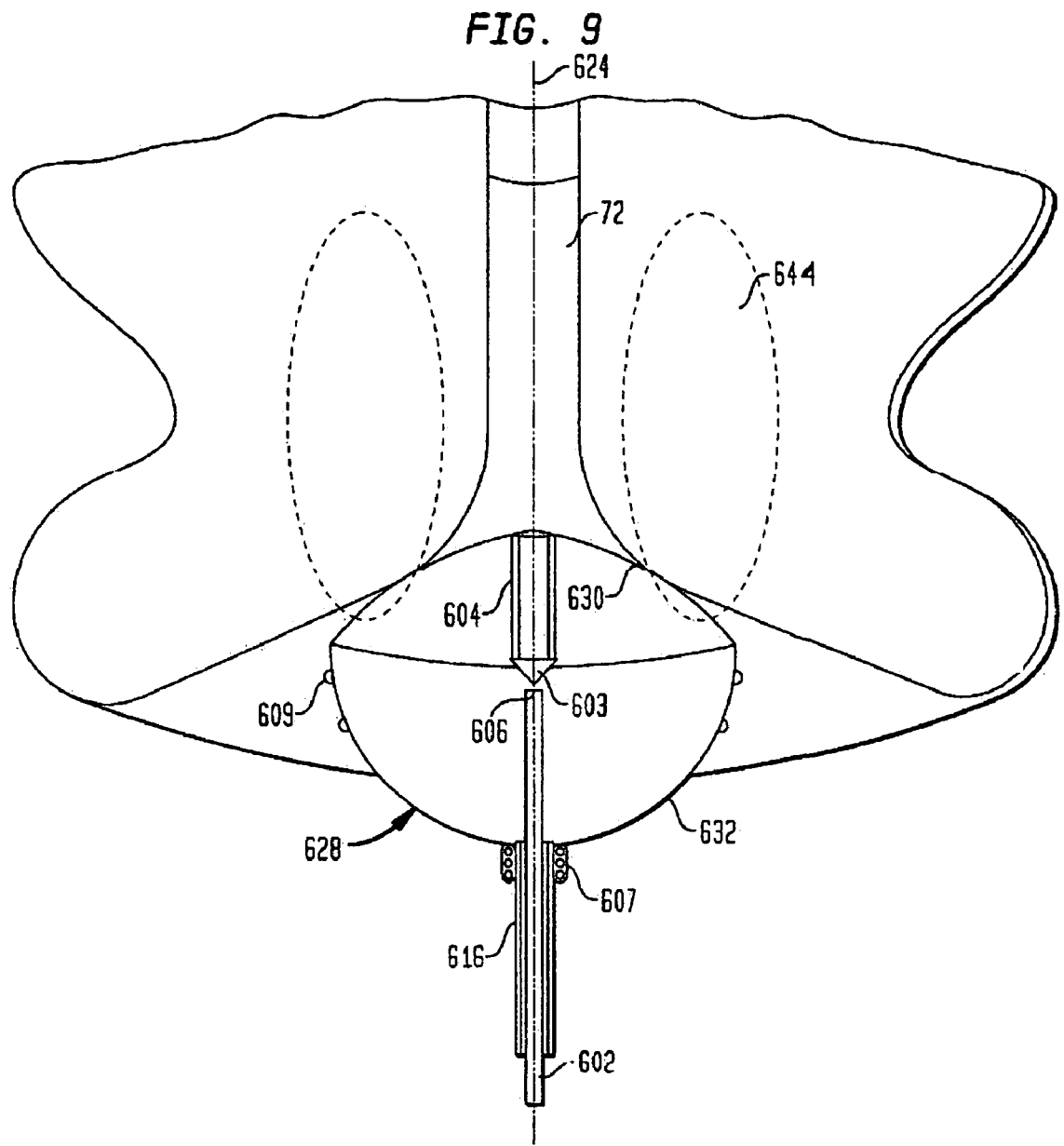
FIG. 9 is a view similar to FIG. 1, but depicting apparatus according to yet another embodiment of the invention.

Apparatus according to a further embodiment includes a reflector structure incorporating single balloon 628 having an active region 632 formed from an optically-reflective material such as a metalized polymer film. The forward wall 630 of balloon 628 is formed from a material which is transparent or translucent to optical radiation in a predetermined band of wavelengths as, for example, red or infrared light. An optical wave guide in the form of a fiber optic 602 extends through the probe structure to the proximal end of the probe structure (not shown). A source reflector 603 is mounted within the first balloon on a support 604 mounted to the forward wall 630 so that when the first balloon is in the inflated condition as shown in FIG. 9, the reflector is aligned with the distal end 606 of the fiber optic. In use, the interior space within the first balloon is filled with a fluid such as a gas transparent to the optical radiation to be applied. The proximal end of fiber optic 602 is connected to a laser or other source of light such as a red or infrared emitting laser. Light transmitted through the fiber optic impinges on source reflector 603 and is redirected from the source reflector onto the active region 632 of the inflatable reflector structure. As in the embodiments discussed above using ultrasonic energy, the reflected light is focused or directed into a loop-like path encircling the central axis 624 and is directed into the wall of the heart in a loop-like region 644 surrounding the central axis 624 and surrounding the ostium of the pulmonary vein. Here again, energy is applied to the entire loop-like region simultaneously.

The variations discussed above with reference to ultrasonic energy application can be used in a generally similar manner for application of optical energy. For example, the active region of the reflector structure may be arranged to focus the optical energy or to redirect it in a substantially collimated beam having the cross section of a hollow cylinder. Also, some focusing can be performed by the source reflector 603 or by a lens (not shown) surrounding the source reflector. In a further variant, the acoustical emitters discussed above with reference to FIGS. 1-8 can be replaced by acoustic wave guides in the probe structure for conducting ultrasonic energy from a sonic source at the proximal end of the probe structure to the reflector structure. Such an arrangement can include a source reflector similar to the optical source reflector 603 of FIG. 9 for directing the ultrasonic energy radially outwardly.

The guide catheter and anchor illustrated in FIG. 1 may be omitted as shown, for example, in FIGS. 5, 6 and 8. Also, a guide catheter may be employed without an anchor. Desirably, placement of the reflector structure in the appropriate location on the heart wall is verified by imaging and/or location-finding techniques before energy is applied to perform the thermal treatment. By way of example, some portions or all of the probe structure may be formed from a material which is visible in an imaging technique such as, for example, a radiopaque material for use in fluoroscopic, CAT or conventional X-ray imaging. Alternatively, the reflector structure itself is visible in an imaging modality. For example, a balloon filled with air or other gas will be readily visible in a magnetic resonance imaging procedure or in an ultrasonic imaging procedure, whereas a balloon filled with a liquid X-ray contrast agent is visible using fluoroscopy.

Thermal treatment of tissues can be monitored using magnetic resonance measurement or imaging. To facilitate such techniques, the probe structure may carry a small antenna 607 for receiving magnetic resonance signals from tissues surrounding the balloon. Alternatively or additionally, a local antenna 609 may be formed on the surface of a balloon included in the reflector structure. Such local antennas are connected by leads (not shown) extending to the proximal end of the probe structure which in turn are connected to the RF signal receiver of a magnetic resonance measurement or imaging device. Use of such a local antenna provides magnetic resonance signals from the tissue adjacent the balloon with a relatively high signal to noise ratio and thus facilitates the magnetic resonance measurement or imaging process.

Figure 10:
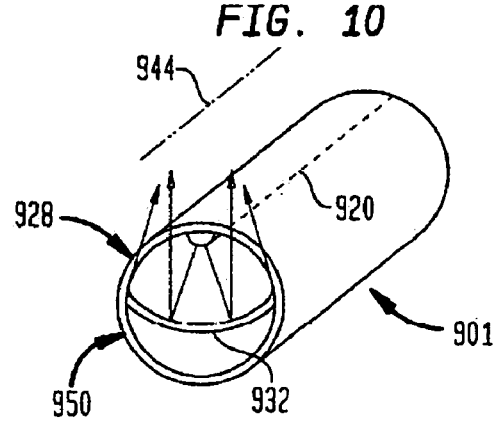
FIG. 10 is a fragmentary, diagrammatic perspective view depicting apparatus according to a further embodiment of the invention.

In the embodiments discussed above, the apparatus acts to direct the applied energy into an annular region. However, in further embodiments of the invention, the reflector structure may direct the energy into a region of a different shape. For example, an elongated reflector structure extending lengthwise along a dual-lumen catheter 901 (FIG. 10) has a first chamber 928 filled with a liquid and a second chamber 950 filled with a gas, so as to form a reflective active region 932 at a wall between these chambers. These features extend lengthwise along the catheter. An elongated emitting element 920 is arranged to direct ultrasonic energy onto the active region, so that the energy will be focused onto an elongated focal region 944 extending parallel to the catheter. In still further embodiments (not shown) the emitting element and reflector structure may be arranged similarly to those discussed above with reference to FIGS. 1-9, but may have shapes other than surfaces of revolution so as direct the energy into a non-circular region. The focal region need not form a closed annulus or loop, but instead may form a partial loop or other elongated path, a spot, or any arbitrary shape. To provide a partial loop such as an arcuate focal region, a shield may be mounted alongside the emitting element in a structure as shown in any of FIGS. 1-9, so that the shield extends generally parallel to the central axis of the emitting element and blocks emission of energy in certain radial directions. Such a shield may be mounted in a fixed position relative to the remainder of the device, or else may be rotatable around the axis by a cable extending through the probe structure, so that the position of the shield may be varied. The reflectivity of the active region in the reflector structure may be selectively controllable in each of several zones distributed around the axis. For example, the second balloon 50 of FIG. 1 may have its interior space 52 subdivided into several zones spaced circumferentially around the central axis, each such zone being connected to a separate lumen so that each zone can be independently inflated with either a liquid or a gas. The active region 32 or interface with the first balloon will be non-reflective in those zones where the second balloon contains a liquid, but will be reflective in those zones where the second balloon contains a gas. In still other embodiments, the emitter may have a plurality of signal electrodes spaced around its circumference, and leads may be provided for independently applying excitation signals to the electrodes so as to actuate the emitter over any selected part of its circumference.

Figure 11:
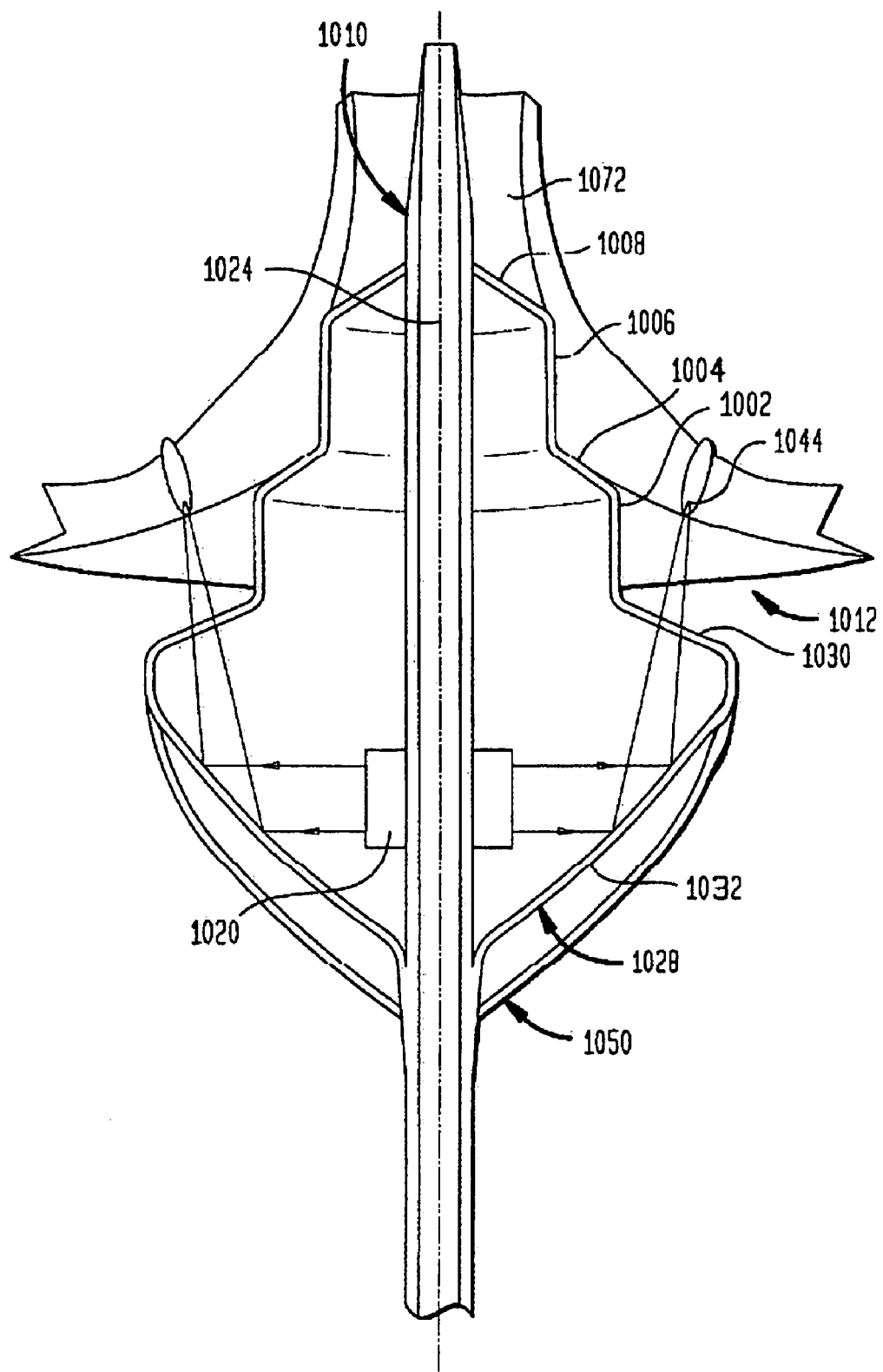
FIGS. 11 and 12 are fragmentary, diagrammatic sectional views depicting apparatus according to further embodiments of the invention.

In the embodiments discussed above with reference to FIGS. 1-9, the forward-facing transmissive wall 30 of the first or structural balloon 28 abuts the tissue of the heart wall when the apparatus is in the operative condition. This abutment holds the expansible structure at a known location relative to the tissue to be ablated and helps to assure that the focal location will lie at the desired depth relative to the surface of the heart wall. However, it is desirable to provide the layer of a fluid medium between the transmissive wall and the surface of the tissue at the ablation location. As seen in FIG. 11, the first or structural balloon 1028 has a transmissive wall 1030 in the form of an annulus surrounding central axis 1024. An abutment projection 1002 extends forwardly from the transmissive wall on the inside of the annulus, adjacent central axis 1024. A generally cylindrical locating projection 1006 extends forwardly from the abutment wall 1004. Locating projection 1006 has a conical lead-in wall 1008 at its forward end. In the embodiment illustrated, the abutment projection 1002 and locating projection 1006 are formed as portions of the first or structural balloon 1028. This balloon is mounted on a carrier catheter 1010 adjacent the distal end of the carrier catheter.

As in the embodiments discussed above with reference to FIG. 1, an ultrasonic transducer 1020 is mounted inside the first or structural balloon 1028. A second or reflector balloon 1050 is also carried on catheter 1010. In the expanded, operative condition shown in FIG. 17, structural balloon 1028 is inflated with a liquid such as an aqueous liquid having acoustic impedance close to that of water and bodily tissue. Reflector balloon 1050 is inflated with a gas having acoustic impedance substantially lower than that of the liquid in the structural balloon, so as to form an acoustic reflective interface at the common wall 1032 separating the interior spaces of these balloons. Thus, balloons 1028 and 1050 cooperatively form an expansible reflector structure.

Carrier catheter 1010 is advanced into the heart and the distal tip of the carrier catheter is threaded into a pulmonary vein 1072. The locating projection 1006 seats in the lumen of the pulmonary vein and centers the assembly with respect to the ostium of the pulmonary vein. As the physician urges the carrier catheter 1010 forwardly, the abutment wall 1004 engages the tissue immediately surrounding the opening of the pulmonary vein. The abutment locates the expansible reflector structure and, hence, the reflecting interface 1032 at a predetermined location in the forward-to-rearward or distal-to-proximal direction along axis 1024, leaving a space 1012 between transmissive surface 1030 and the tissue surface at the focus 1044. The space is filled with the blood present in the heart. The acoustic energy from transducer 1020 is reflected at interface 1032 and focused by the reflective interface onto the loop-like focal region 1044 in substantially the manner discussed above with reference to FIG. 1. Because space 1012 is filled with blood having acoustic impedance and acoustic velocity close to the aqueous fluid within balloon 1028, the space does not materially affect the ultrasonic transmission. However, the presence of a layer of liquid at the surface of the tissue helps to assure reasonably uniform heat transfer from the tissue surface.

The particular abutment structure shown in FIG. 11 is only exemplary. For example, abutment projection 1002 and guide projection 1006 need not be formed integrally with the structural balloon. These elements can be formed as separate balloons carried on carrier catheter 1010 or otherwise physically linked to the expansible structure defining the reflective surface. Also, the abutment structure need not provide a continuous abutment wall encircling the central axis 1024. For example, the abutment structure can be formed by a set of arms or other mechanical elements, which project outwardly from the carrier catheter in the operative condition. Alternatively or additionally, abutment elements can be provided around the outside of the transmissive wall, i.e., further from the central axis than the transmissive wall.

Figure 12:
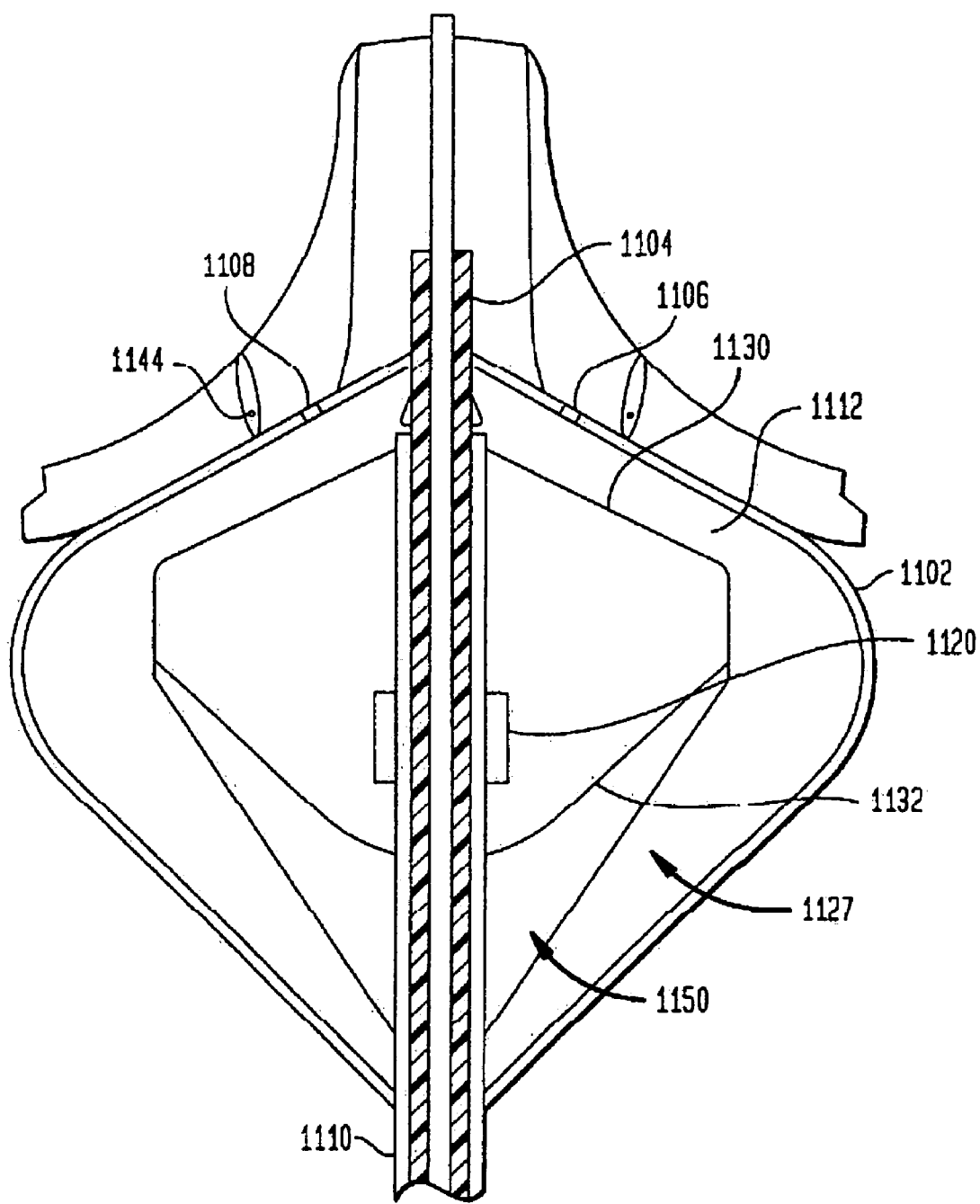

The embodiment depicted in FIG. 12 includes an expansible reflector structure 1127 with a structural balloon having a transmissive surface 1130, and with a reflector balloon 1150, similar to those discussed above, defining a reflective interface 1132, as well as a sonic transducer 1120. These elements are similar to the corresponding elements of the embodiments discussed above. The expansible reflector structure is surrounded by an expansible basket 1102 formed from a set of wires. The expansible basket may be actuated by an actuator catheter 1104 slidably mounted in the carrier catheter 1110. By retracting the actuator catheter 1104 rearwardly relative to the carrier catheter 1110, the expansible basket may be brought to the expanded condition illustrated. The basket structure holds the expansible reflector structure 1127 at a predetermined distance from the surface of the cardiac wall and, thus, serves as a standoff, so as to provide a space 1112 between the transmissive wall and the tissue. Preferably, the basket structure includes relatively few wires extending across the path or ablation region, and these wires are of the smallest practical diameter, so that they do not materially interfere with the ablation procedure.

The basket structure also may carry sensing electrodes 1106 and 1108. For example, each of the wires may be covered with a substantially continuous electrical insulating coating, except at those locations which are to serve as electrodes. The wires are connected by conductors (not shown) to conventional electrophysiologic potential monitoring equipment. Although only two electrodes are depicted in FIG. 18, the set of electrodes used for physiologic potential monitoring may include more than two electrodes.

Electrophysiologic potential monitoring can be used to monitor and to control the ablation procedure. The electrophysiologic potential propagates along the wall of the heart. Thus, electrodes disposed at different locations on the cardiac wall will be exposed to differing potentials at any given time. The pattern of change in these differences represents the propagating electrophysiologic potential. If the ablation forms a complete conduction block extending along a closed, loop-like path, the region inside of such loop-like path will be isolated from the potential propagating in the rest of the heart. Electrodes 1106 and 1108 are disposed at locations closer to the central axis 1124 than the ring-like focal region 1144, so that these electrodes will engage the cardiac tissue at locations inside of the ring-like ablation region formed by the focused energy. Prior to ablation, the electrical signal appearing across these two electrodes will have a component having a fixed phase relationship to the electrophysiologic signal in the rest of the heart. The potential propagating in the heart outside of the ablation region can be detected by further electrodes (not shown), or by conventional electrocardiographic ("ECG") techniques. Once a complete conduction block has been formed, it encircles the region contacted by the electrodes and electrically isolates such region from the remainder of the heart. The signal appearing across electrodes 1106 and 1108 will change and will no longer have a component linked to the signal in the rest of the heart. This change can be detected during application of the sonic energy, and application of the sonic energy can be terminated once a complete conduction block has been achieved, as shown by the change in the electrical signals. Alternatively, the ultrasonic or other energy used for ablation can be applied for a first predetermined period, and then terminated. Following this first period, the electrophysiologic potential can be monitored. If the block is complete, the process is terminated. If not, the process is repeated.

Figure 13A:
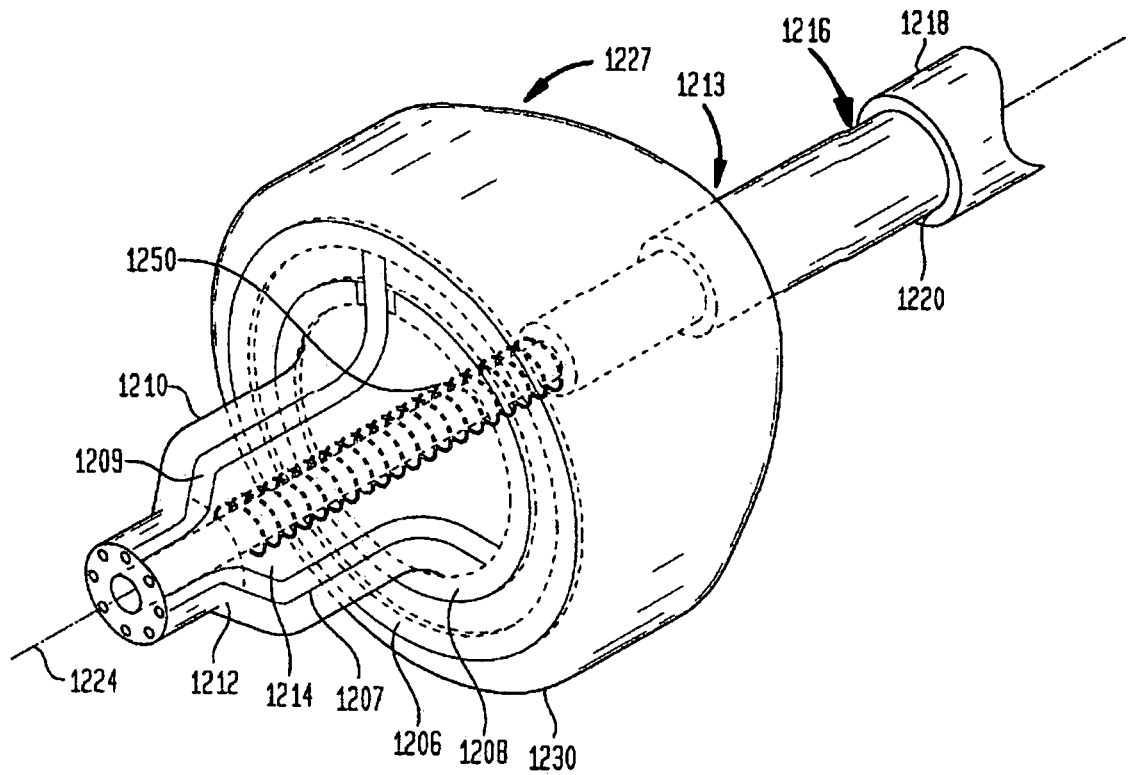
FIG. 13A is a fragmentary perspective view depicting apparatus according to yet another embodiment of the invention.

Apparatus according to a further embodiment of the invention (FIG. 13A) includes an expansible balloon structure 1227 having a pair of ring-like monitoring electrodes 1206 and 1208 disposed on the forward or transmissive wall 1230. These electrodes desirably are formed by thin metallic coatings, as, for example, sputtered, electroless-plated or electroplated gold. In this embodiment, the forward or transmissive wall 1230 of the balloon structure is arranged to contact the cardiac wall, at least in the region encompassed by electrodes 1206 and 1208. A guide projection 1210 similar to the guide projection 1106 discussed above with reference to FIG. 11 projects forwardly from wall 1230 and enters into the ostium of the pulmonary vein during use.

The distal end 1212 of the expansible balloon structure, in this case the distal end of guide projection 1210, is mechanically connected to a guide catheter 1214 slidably mounted in carrier catheter 1216. The proximal end 1213 of the expansible balloon structure is mechanically connected to the carrier catheter 1216. Both of these catheters extend rearwardly to the proximal end of the probe (not shown). Electrodes 1206 and 1208 are connected by conductors 1207 and 1209 extending along the balloon structure to conductors (not shown) extending within guide catheter 1214. These conductors convey the electrical signals to electrophysiologic monitoring instruments (not shown) at the proximal end of the probe, outside of the patient's body.

The guide catheter and carrier catheter also can be manipulated during use to facilitate collapse of the balloon structure after operation and withdrawal of the balloon structure. Typically, the balloon structure is supplied by the manufacturer in a fully-collapsed condition, so that the structure has a small diameter. In this condition, the carrier catheter 1216 and some portion or all of the balloon structure 1227 may be housed within the interior bore of an introducer catheter 1218. The introducer catheter has an opening 1220 at the distal end of the internal bore. The introducer catheter also extends to the proximal end of the probe. After the introducer catheter has been placed within the heart, carrier catheter 1216 and guide catheter 1214 are advanced relative to the introducer catheter to move the balloon structure 1227 out of the introducer catheter. The balloon structure is expanded and inflated to the operative condition illustrated in FIG. 13A. During inflation, as the balloon structure moves from the collapsed condition to the expanded condition, the distal end 1212 and, hence, guide catheter 1214 are drawn rearwardly or proximally relative to the proximal end 1213 and carrier catheter 1216. After the ablation procedure, the balloon structure is collapsed by withdrawing fluid from the interior of the structure. During collapse, the physician can manipulate the guide catheter and carrier catheter, so as to move the guide catheter and distal end forwardly or distally relative to the proximal end 1213 and carrier catheter, as by advancing the guide catheter 1214 relative to the introducer catheter 1218, while leaving the carrier catheter in fixed position relative to the introducer catheter; by retracting the carrier catheter while leaving the guide catheter in fixed position, or by moving both the guide catheter and the carrier catheter. This forces the distal end of the balloon away from the proximal end along the central axis 1224, which promotes orderly collapse of the balloon structure into a small, compact unit with minimal wrinkling of the balloon wall. The physician also may twist the guide catheter relative to the carrier catheter so as to twist the balloon structure during collapse. In a further variant, the balloon can be twisted without deliberate axial elongation. After collapse of the balloon structure, the balloon structure can be withdrawn back into the interior bore of introducer catheter 1218 by pulling the carrier catheter 1216 rearwardly. Minimizing wrinkling and providing an orderly collapse facilitates re-entry of the balloon structure into the distal end of the introducer catheter. Moreover, even if the balloon structure cannot be drawn back into the introducer catheter, it is still desirable to provide a relatively smooth structure after collapse, so as to facilitate withdrawal of the apparatus from the patient's body.

In a variant of this approach, a resilient element such as a small coil spring 1250 may be provided within the balloon structure. The resilient element is arranged so that it tends to force the distal end 1212 of the balloon distally or forwardly relative to the proximal or rearward end 1213 of the balloon. The resilient disposed within the balloon structure is compressed between the distal end of the balloon and the proximal end when the balloon structure is inflated. In the embodiment illustrated, the proximal end of the coil spring rests against the distal end of the transducer 1220, which in turn is mechanically linked to the proximal end 1213 of the balloon structure and to the carrier catheter 1216. When the fluid pressure within the balloon structure is released and the structure deflates, resilient element or spring 1250 will force the distal end of the balloon away from the proximal end. Other forms of resilient element may be employed, as, for example, a compressible, elastomeric tube surrounding the guide catheter. The use of a resilient element makes it unnecessary to transmit motions through the carrier catheter and guide catheter during the deflation process. This facilitates the use of a relatively soft, limber carrier catheter, with a similarly limber guide catheter, or with no guide catheter at all. This, in turn, can facilitate positioning of the apparatus within the heart. The carrier catheter may have a highly flexible region forming a flexible joint disposed immediately proximal to the balloon.

Figure 13B:
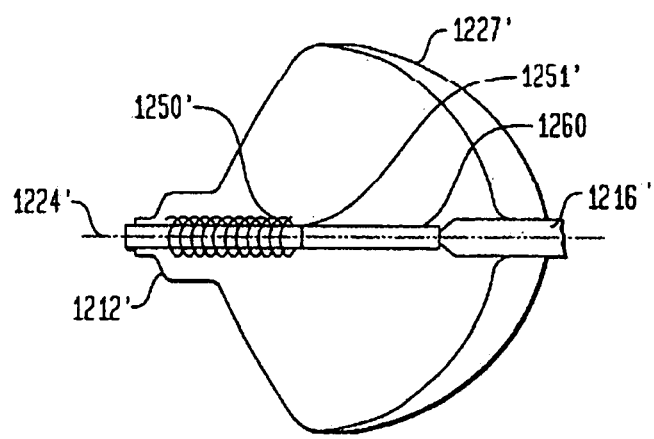
FIG. 13B is a fragmentary, diagrammatic sectional view depicting apparatus according to another embodiment of the invention.

In a further variant, the spring may be arranged so that the coils of spring 1250' engage one another so as to form a column which has appreciable stiffness in bending transverse to the axis of the spring when the spring is in the axially-collapsed or compressed state depicted in FIG. 13B. For example, the coils of a conventional coil spring may be formed from square wire. Alternatively, the coils may be arranged to nest fully or partially within one another when the spring is collapsed axially. Such a spring is commonly referred to as a "volute" spring. The proximal end of the spring is mechanically coupled to the carrier catheter 1216. In the arrangement illustrated, the proximal end 1251' of the spring is mounted to the distal end of an elongated energy emitter such as an ultrasonic transducer as discussed above, and the proximal end of the emitter is mechanically connected to the carrier catheter 1216'. Preferably, the spring is substantially coaxial with the emitter, and the axes of these components coincide with the central axis 1224' of the carrier catheter distal end. The distal end 1253' of the spring is connected to the distal end 1212' of the balloon, whereas the proximal end 1213' of the balloon is connected to the carrier catheter. The spring thus resists movement of the distal end of the balloon relative to the proximal end transverse to the central axis, and maintains the orientation of the balloon relative to the carrier catheter and, particularly, relative to the emitter. This helps to maintain the shape of a reflecting surface defined by the balloon during use, and also helps to maintain alignment between the balloon and the emitter. In the embodiment of FIG. 13B, the spring is used without the guide catheter 1214 shown in FIG. 13A.

Figure 14:
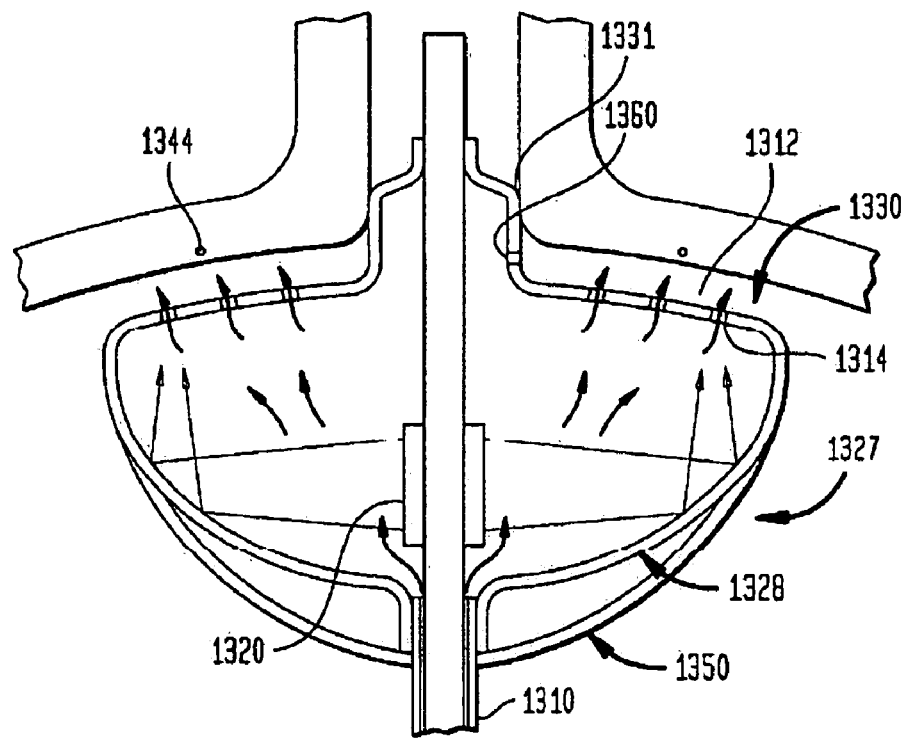
FIGS. 14 and 15 are fragmentary, diagrammatic sectional views depicting apparatus according to further embodiments of the invention.
Figure 20:
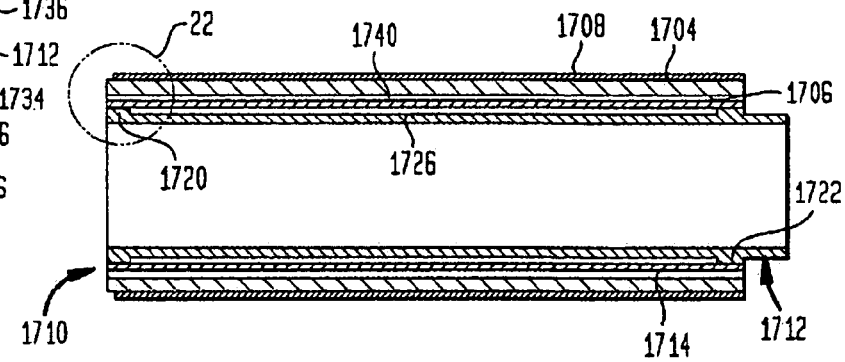
FIG. 20 is a sectional view of the transducer of FIG. 19.
Figure 21:
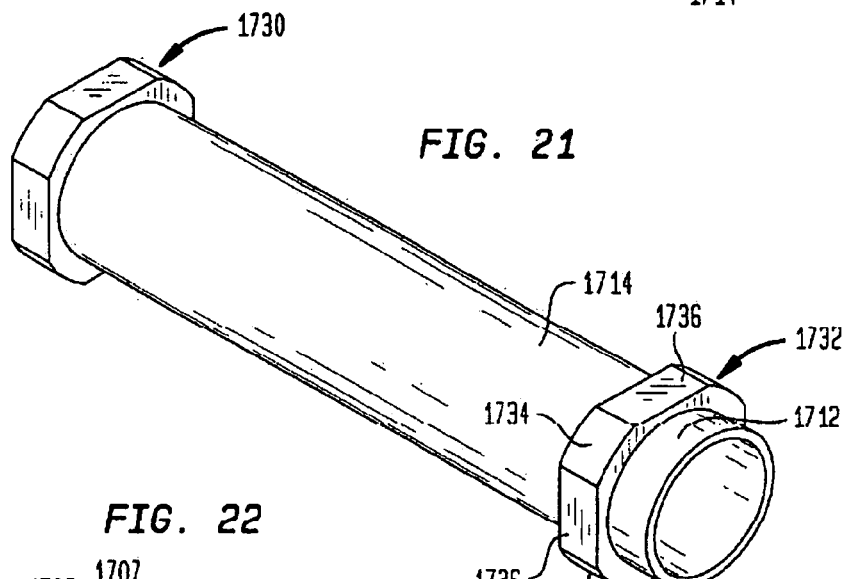
FIG. 21 is a perspective view of a part of the transducer of FIGS. 19 and 20.

Apparatus according to a further embodiment of the invention (FIG. 14) includes an expansible structure 1327, including a first or structural balloon 1328 and a second or reflector balloon 1350, similar to those discussed above. The structural balloon has a forwardly-facing transmissive wall 1130. A guide structure 1331 projects from the forward or transmissive wall 1330. However, the guide structure does not limit forward motion of the inflated balloon structure. To provide a stand-off or spacing 1312 between the transmissive wall 1330 and the tissue at the focal location, the transmissive wall 1330 is made porous. Thus, the transmissive wall has an array of ports 1314 distributed over the transmissive wall. Preferably, the ports are provided in the portion of the transmissive wall that immediately overlies the annular focal location 1344, or in neighboring areas of the transmissive wall. Although ports 1314 are shown in FIG. 20 as discrete holes for clarity of illustration, the ports may be microscopic. Merely by way of example, suitable ports can be formed in the wall of a polyethylene tereptha-late ("PET") balloon by laser ablation of the balloon wall. A biocompatable inflation liquid, as, for example, an isotonic saline solution, is introduced into the structural balloon 1328 through a lumen in the probe structure, as, for example, the lumen of the carrier catheter 1310. The fluid flows through the interior space of the structural balloon and out through ports 1314, so as to form a liquid layer between the transmissive wall and the cardiac tissue at focal region 1344. Thus, even though the physician urges the balloon assembly forward by urging the carrier catheter 1310 forward, the transmissive wall does not contact the cardiac tissue at the focal region. Nonetheless, the reflective interface is maintained at a precise location relative to the surface of the cardiac tissue.

Ports 1314 desirably have substantial resistance to flow, so that a substantial internal pressure is maintained within the interior space of structural balloon 1328 at a moderate flow rate of liquid through the balloon. The flowing liquid desirably is introduced into the balloon adjacent ultrasonic emitter or transducer 1320, so that some or all of the flowing liquid will pass over or through the transducer and maintain the temperature of the transducer within desired limits.

In a variant of this approach, one or more ports 1360 can be provided on guide catheter 1331 or on a guide member of the structural balloon which projects distally of wall 1330. These ports desirably also communicate with the interior space of the structural balloon, or with a lumen (not shown) in a catheter, so that liquid can be supplied to the ports either through structural balloon 1328 or through a separate lumen of the structural balloon. Where the focal region is annular, the port 1360 desirably is located within the annulus defined by the focal region, so that fluid flowing outwardly from the port over the transmissive wall will pass across the focal region and maintain a fluid layer between the transmissive wall and the tissue at the focal region.

A transmissive liquid layer also can be used with energy other than ultrasonic energy, provided that the fluid used to maintain the layer is transmissive to the energy applied. For example, where light energy is applied, the fluid layer should be transparent.

Figure 15:
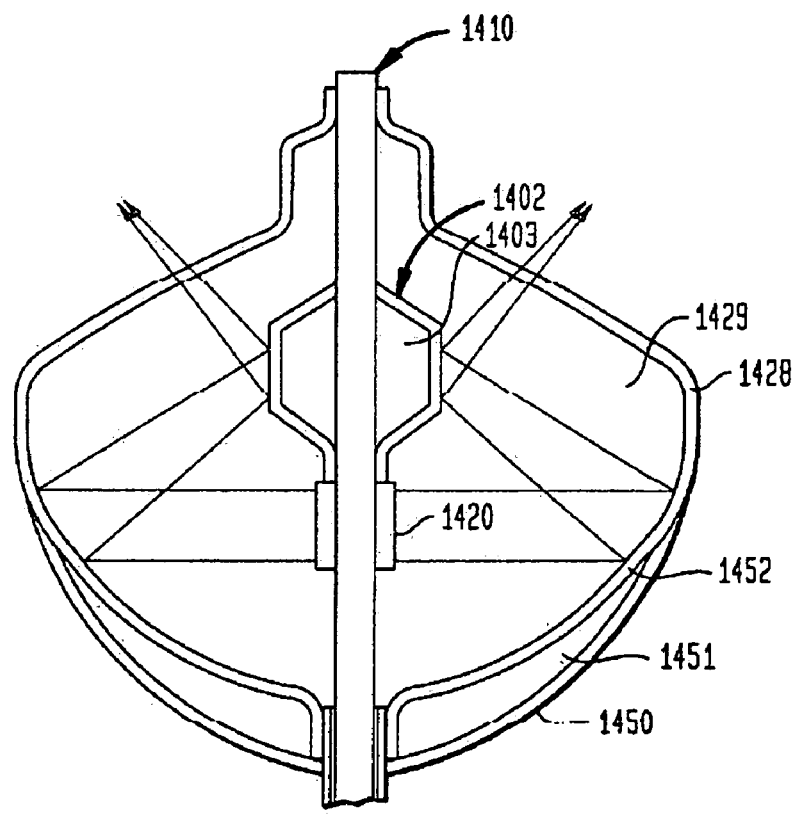

In the embodiment of FIG. 15, the expansible structure incorporates a structural balloon 1428 having an interior space 1429, which, in operation, is filled with a liquid and also includes a reflector balloon 1450 having an interior space 1451 filled with a gas during operation as described above, so as to provide a reflective interface or active region at wall 1452. The expansible structure also includes a reflective redirecting element 1402 in the form of a further balloon having an interior space 1403, which is filled with a gas during operation. This forms an additional reflective interface 1404 at the wall separating the interior space 1403 of balloon 1402 from the interior space 1429 of the structural balloon. The redirecting element 1402 is mounted on the probe structure 1410, so that in use, with all of the balloons inflated, the redirecting element 1402 is juxtaposed with the active region 1452. Energy reflected from the active region will be directed onto the additional reflective interface 1404 defined by the redirecting element 1402. The energy is then reflected from this interface onto the focal region.

The redirecting element allows the use of a reflector balloon and active region having a more compact configuration. Although the use of a redirecting element has been described with reference to ultrasonic energy, the same principle can be applied to light or other electromagnetic energy. In this case, the redirecting element may be a balloon having a metallic or other light-reflecting surface. The reflective interface defined at the redirecting element may be shaped so that it further focuses or collimates the energy reflected from it. In a further variant, energy is reflected from the redirecting element back onto an additional portion of the reflective interface defined by the same elements which define the active surface, as, for example, onto a further portion of the reflective interface defined between balloons 1450 and 1429 in FIG. 15. Thus, the energy passes through three separate reflections in passing from the emitter to the tissue. This approach can be combined with additional focusing or collimating elements, such as refractive elements.

Figure 16:
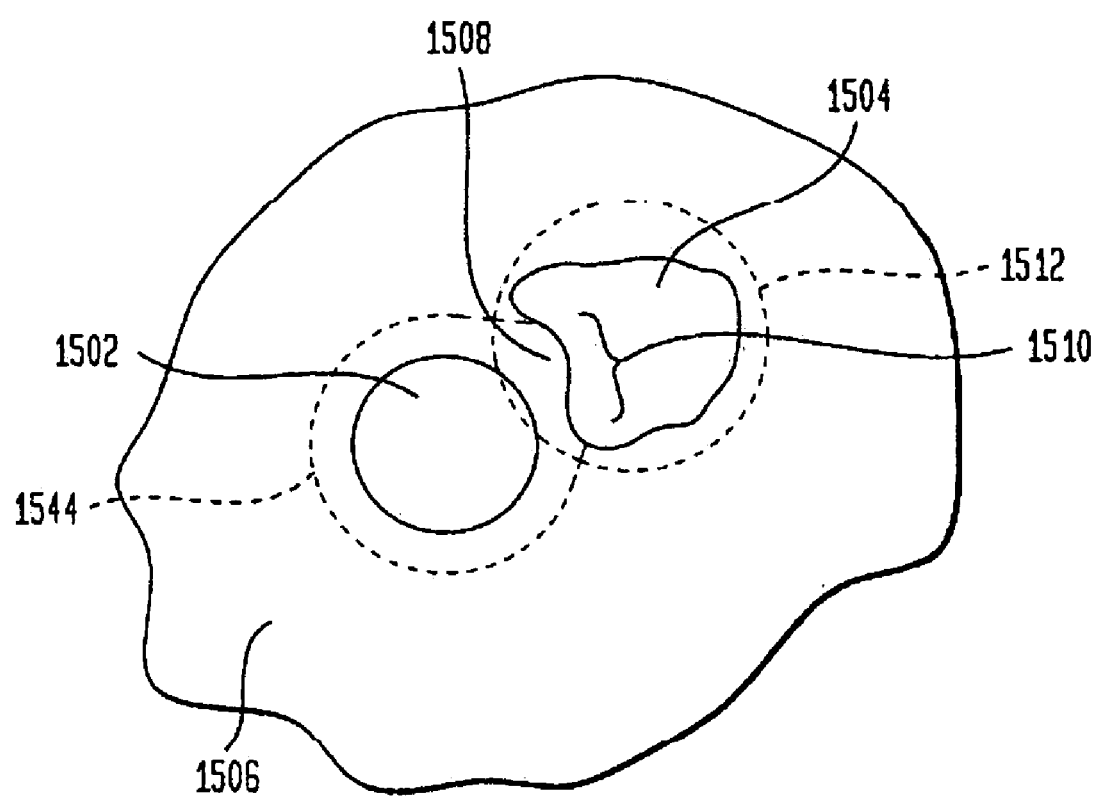
FIG. 16 is a diagrammatic plan view depicting a portion of the interior wall of a cardiac atrium.

In some instances, the topography of the cardiac wall may make it difficult to ablate a fully-closed loop around the ostium using forwardly-directed energy focused along a loop-like path, as discussed above with reference to FIG. 1. For example, as seen in FIG. 16, the ostium 1502 of the pulmonary vein is disposed adjacent the atrial appendage 1504. The atrial appendage 1504 forms a pocket or recess communicating with the interior of the atrium. Stated another way, as seen from within the atrium, as in FIG. 16, the tissue of the cardiac wall is recessed within appendage 1504. The tissue in recess 1504 lies further from the viewer, as seen in FIG. 16, than the tissue in the main region 1506 of the atrial wall. There is a relatively narrow ridge of tissue 1508 at the level of the main region 1506 extending between the ostium 1502 and the opening of atrial appendage 1504. If energy is focused at an appropriate depth to ablate tissue along a loop-like path 1544 on the main region 1506 of the atrial wall, it will not successfully ablate tissue within recess 1504. If the path extends over the opening of atrial appendage 1504, ablation will not occur along this region 1510 of the path. To form a complete, closed loop, an additional conduction block may be formed along a further path 1512 extending around the atrial appendage and intersecting path 1544. Thus, the region of path 1544 where ablation occurs (the region other than region 1510) forms a first conduction block extending partially around the ostium of the pulmonary vein 1502; whereas, the region along path 1512 forms a second conduction block extending around the opening of the atrial appendage 1504. These conduction blocks intersect one another and form a substantially closed conduction block encompassing both the opening of the atrial appendage and the ostium of the pulmonary vein. A second conduction block may be formed by ablation using the apparatus discussed above, or by other, conventional techniques. In a similar manner, a conduction block formed using the apparatus and methods discussed herein can cooperate with natural conduction blocks, such as the openings of valves in the heart, or with other medically created conduction blocks, so as to provide a composite, closed loop-like conduction block. In one such example, where two pulmonary veins are disposed closed to one another, a partial loop-like conduction block may be formed around the ostium of each pulmonary vein using the apparatus and methods discussed above, so that the two partial conduction blocks intersect one another.

Apparatus according to a further embodiment of the invention (FIGS. 17 and 18) includes an elongated probe incorporating an introducer catheter 1610 having an interior bore with an opening 1612 at its distal end and a skirt member 1614 slidably mounted within the interior bore of the introducer catheter. The skirt member includes a tubular body 1616 having an internal bore. This body may be in the form of a further elongated catheter extending all the way to the proximal end of the probe, so that it can be manipulated directly from outside of the patient's body during use. Alternatively, the body 1616 may be linked to a guide wire or other member extending within introducer catheter 1610 and capable of transmitting forward and rearward forces. Skirt member 1614 defines a central axis 1618, referred to herein as the "skirt axis." The skirt member includes a plurality of limbs 1620 disposed around the skirt axis. Each limb has a proximal end 1622 pivotably connected to the body 1616 of the skirt member, and has a distal end 1624 remote from the body. The limbs are movable between the collapsed condition seen in FIG. 18, in which the distal ends of limbs 1620 lie relatively close to the skirt axis 1618, and an expanded condition seen in FIG. 17. In the expanded condition, the distal ends 1624 of the limbs are disposed further from the skirt axis than the proximal ends 1622, so that each limb slopes in the radially-outward direction, away from the skirt axis in the distal direction. The apparatus further includes a carrier catheter 1626 and a balloon 1628 mounted on the carrier catheter. The carrier catheter, or another catheter included in the probe, has an inflation conduit communicating (not shown) with the interior of the balloon, so that the balloon can be inflated and deflated. The particular balloon 1628 illustrated in FIGS. 17 and 18 forms part of an expansible structure, as discussed above, for directing energy onto the wall of an internal organ. Carrier catheter 1626 is slidable in the forward and rearward (distal and proximal) directions relative to skirt member 1614 and introducer catheter 1610.

When the apparatus is initially supplied, the balloon 1628 is surrounded by the limbs of the skirt member and is disposed inside the introducer catheter 1610. After the apparatus has been threaded into the heart or other organ to be treated, carrier catheter 1626 is advanced relative to the skirt member and relative to the introducer catheter, and the balloon is inflated. In this condition, the distal ends of the limbs surround the carrier catheter 1626.

After performing the desired treatment, the apparatus is brought to the condition illustrated in FIG. 17. In this condition, the limbs of the skirt member surround at least the proximal end of the balloon. Desirably, the balloon and carrier catheter are retracted further relative to the skirt member, so that the limbs substantially surround the balloon. While the limbs are in position around the balloon, the balloon is deflated and the carrier catheter and skirt member are retracted relative to the introducer catheter, so that the limbs and balloon enter into the introducer catheter. During this motion, the limbs help to guide the balloon into the bore of the introducer catheter.

In a variant of this approach, the introducer catheter is omitted and the skirt member is used as an introducer catheter. The distal ends of the limbs are secured in the retracted position by frangible or water-soluble elements (not shown) connecting the distal ends to one another or by an elastic member, such as an elastic band surrounding the limbs or the like. Here again, after use of the balloon, at least the proximal end of the balloon and desirably the entire balloon, is seated within the limbs of the skirt member. In this case, the limbs of the skirt member may remain partially expanded. However, the limbs will serve to guide the deflated balloon through the vascular system or other tissues of the subject during withdrawal. The skirt member and the carrier catheter may be retracted together to withdraw the apparatus from the patient.

Figure 22:
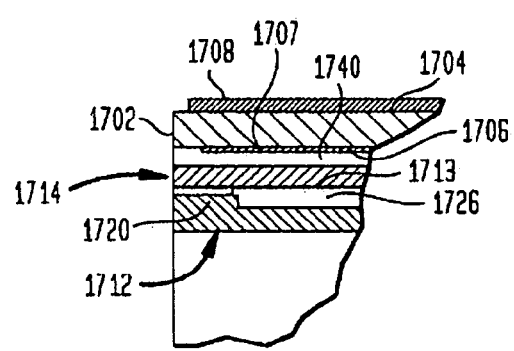
FIG. 22 is a fragmentary view on an enlarged scale of the area indicated in FIG. 20.

A preferred ultrasonic transducer or emitter usable in the present invention is depicted in FIGS. 19-22. This transducer is further described in U.S. Pat. No. 6,763,722, the disclosure of which is hereby incorporated by reference herein. The emitter includes an active piezoelectric element 1702 in the form of a thin cylindrical tube having an exterior or front surface 1704 and an interior or rear surface 1706. An electrode 1708 forms the front surface 1704 of the piezoelectric element, and a similar electrode 1707 forms the rear surface. The thickness of the electrode is greatly exaggerated in FIGS. 20 and 22 for clarity of illustration. In practice, the electrode preferably is formed by a thin metallic coating, such as a plated or sputtered coating of metal on the order of a few thousand Angstroms thick overlying the actual piezoelectric material. An internal structure 1710 includes an inner support tube 1712 and an outer support tube 1714. Support tubes 1712 and 1714 desirably are formed from a metallic, electrically conductive material. As best seen in FIG. 22, inner support tube 1712 has an outwardly projecting shoulder 1720 at one end. A similar shoulder 1722 is provided at the opposite end. Outer support tube 1714 has a cylindrical internal bore. Shoulders or rings 1720 and 1722 fit closely within the cylindrical bore of the outer support tube. Thus, over the major portion of the length of the support structure, between shoulders 1720 and 1722, there is a gap 1726 between the inner surface of outer support tube 1714 and the outer surface of inner support tube 1712. The tubes are sealed to one another at shoulders 1720 and 1722. Gap 1726 is filled with a gas, such as normal room air, at the time the tubes are sealed to one another. This gas remains permanently within gap 1726.

Figure 19:
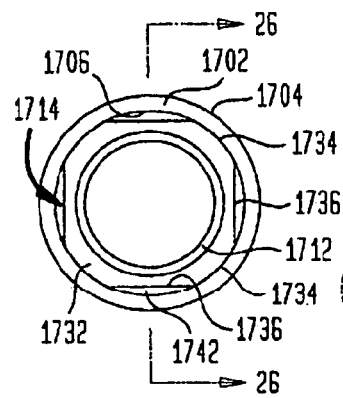
FIG. 19 is an end view of a transducer used in an embodiment of the invention.

Outer support tube 1714 has a pair of outwardly projecting shoulders 1730 and 1732 at the ends of the outer support tube. Each shoulder has arcuate surfaces 1734 connected by flats 1736, so that each shoulder is generally in the form of a square with rounded corners. The arcuate surfaces 1734 are concentric with the main portion of the support tube 1714. Seen in end view, the flats 1736 are tangent to the cylindrical surface of the main portion of the support tube. As best seen in FIG. 19, the tubular piezoelectric electric element 1702 is supported on the arcuate surfaces 1734 of shoulders 1732 and 1730, so that the inner surface 1706 of the piezoelectric element is concentric with the outer surface of support tube 1714, but is spaced apart from the support tube so as to define a space in the form of a tubular passageway 1740 between the outer support tube and the inner or rear surface 1706 of the piezoelectric element. Passageway 1740 is open to the exterior of the transducer through small gaps 1742 defined between the inner surface 1706 of the piezoelectric element and the flats 1736 of the shoulders on the outer support tube.

In operation, the space or passageway 1740 is filled with a liquid. The front surface of the emitter (the front surface 1704 of the active piezoelectric element) is acoustically coupled to the medium which is to receive ultrasonic energy from the emitter.

For example, the emitter of FIGS. 19-22 may be used as the ultrasonic emitter 1758 in the apparatus depicted in FIG. 23A. This apparatus includes a probe structure incorporating a carrier catheter 1760, a structural balloon 1756 having a proximal end connected to the carrier catheter, and a guide catheter 1750 extending through the lumen of the carrier catheter into or through structural balloon 1756. Guide catheter 1750 has an internal lumen 1752 and one or more ports 1754 communicating with the interior space of the structural balloon 1756 adjacent the distal end of this balloon and distal to the transducer 1758. The lumen of the carrier catheter is connected to a source 1761 of a liquid such as an aqueous liquid as, for example, water or saline solution, whereas the lumen of guide catheter 1750 is connected to a drain. The liquid source may include conventional fluid-handling elements as, for example, a reservoir containing a liquid and a pump or gravitational feed arrangement to convey the liquid through the system. The liquid is admitted from carrier catheter 1760 adjacent the proximal end of the balloon through an annular opening close to the proximal end of the transducer, so that the liquid flows generally in the distal direction. The source and drain are arranged to maintain the liquid in the balloon under the desired pressure.

Figure 23:
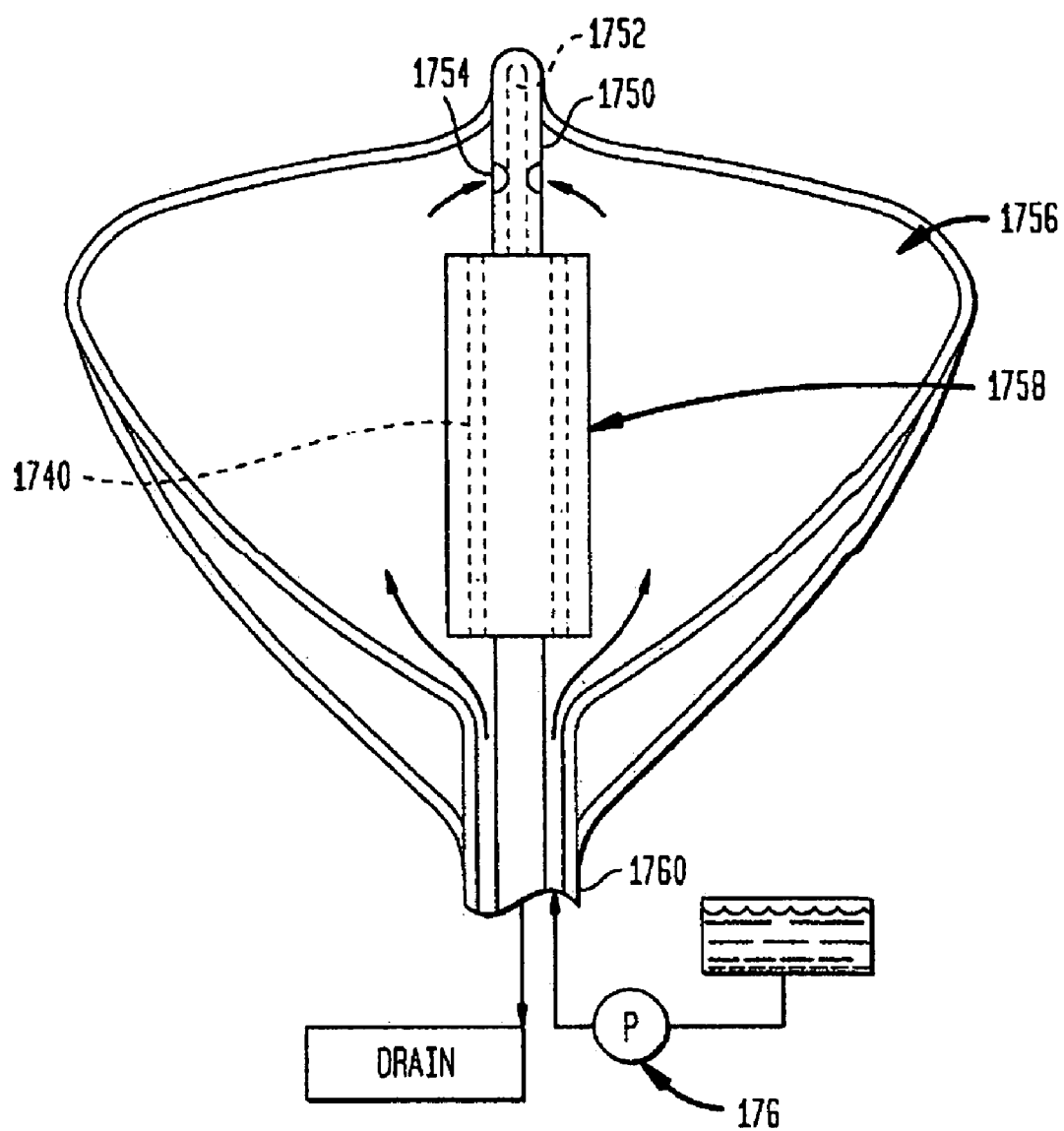
FIG. 23 is a fragmentary sectional view of apparatus according to an embodiment of the invention incorporating the transducer of FIGS. 20-22.

A significant portion of the flowing liquid will pass through the passageway or space 1740 within the transducer. The source and drain connections may be reversed to provide the opposite flow, with liquid admitted through ports 1754 and passing out through the proximal end of the balloon into carrier catheter 1760. Also, the drain may be connected to feed the source, so that the liquid continually recirculates. Additionally, a baffle structure may be provided to direct more of the flowing liquid through passageway 1740. At one extreme, the emitter may be sealingly connected to the carrier catheter 1760 or to the guide catheter 1752, so that liquid can only enter the structural balloon through the passageway 1740 of the emitter, or so that liquid can only leave the structural balloon through passageway 1740. In this manner, all of the fluid passing through the structural balloon is directed through the passageway 1740. In a further variant (not shown), the carrier catheter, or another catheter included in the probe structure, has a liquid-feed lumen and has a liquid-withdrawing lumen. Both of these lumens communicate with the interior of the structural balloon at the proximal end of the balloon. The liquid-feed lumen is connected to fluid source 1761 whereas the liquid-withdrawing lumen is connected to the drain. Thus, the liquid enters and leaves the balloon at the proximal end, near to the opening of passageway 1740 at the proximal end of the emitter. Desirably, the fluid moves at an appreciable velocity, so that some portion of the flowing fluid passes through passageway 1740. In the arrangement of FIG. 23, the front surface of the emitter is in contact with the liquid in the balloon 1756 so that the emitter can radiate ultrasonic energy into the liquid into the balloon; the liquid in the balloon serves as the medium coupled to the front surface of the emitter.

The air or other gas in gap 1726 (FIGS. 20, 22) forms a highly-reflective interface 1713 with the metallic material of the outer support tube 1714. In operation, the emitter is excited by an electrical potential applied between electrodes 1707 and 1708. This potential is applied at a predetermined ultrasonic drive frequency as, for example, about 1-15 MHz. The potential may be applied through electrical conductors (not shown) extending between the proximal end of the probe structure and the emitter, using a conventional ultrasonic-frequency driver (not shown). For example, the conductors may be provided as one or more miniature coaxial cables, each including an inner conductor and an outer conductor or jacket. The jackets of the coaxial cables may be soldered or otherwise bonded to the outer support tube, and hence electrically connected to the inner-surface electrode of the piezoelectric element, whereas the inner conductors may be connected to the outer-surface electrode 1708.

The reflective interface at surface 1713 (FIG. 22) and the outer surface 1704 of the emitter, and the stack of materials between these surfaces, constitute a resonant unit. As the piezoelectric material is excited, it repeatedly grows and shrinks in the forward-to-rearward direction of the stack, i.e., in the direction between surfaces 1704 and 1706 (up and down in FIG. 22). The ultrasonic vibrations propagate through the stack, and are reflected forwardly at the interfaces within the stack and by the interface at surface 1713, at the inner or rear surface of the stack. The dimensions of the various layers in the interior of the stack, between surfaces 1713 and 1704 (including the liquid layer within space 1740) are selected so that the unit is resonant at the drive frequency, and so that the acoustic vibrations are emitted from the resonant unit principally through the front surface 1704 into the medium coupled to the front surface. That is, more energy passes through the interface 1704 at the outer or front surface of the stack than through interface 1713. Although there is some reflectivity at interfaces within the stack, as at the interfaces bounding the liquid passageway 1740, the reflective interface 1713 is effectively exposed to the ultrasonic vibrations in the stack and, thus, plays a substantial role in directing emissions to the front of the stack. The liquid within passageway 1740 effectively cools the piezoelectric element and other elements of the stack. Thus, the transducer element 1702 is cooled at both its front surface and its rear surface. This is in marked contrast to a conventional air-backed transducer. Such a transducer typically has a layer of air directly behind the rear surface of the piezoelectric element and, accordingly, has little or no heat transfer from the rear surface of the piezoelectric element. Surprisingly, an emitter in accordance with this design can convert electrical power to acoustic power radiated into the surrounding medium through the front surface with an efficiency equal to the efficiency of an air-backed emitter. The emitter according to this design, however, provides this efficiency in conjunction with better heat transfer and, hence, can operate at substantially higher power levels than the equivalent air-backed transducer of the same size.

The materials and dimensions of the various layers in the resonant unit desirably are optimized to assure maximum efficiency at the desired operating frequency. Conventional modeling techniques may be employed for such optimization. One such technique is the well-known KLM Model described in Krimholtz et al., "New Equivalent Circuits for Elementary Piezoelectric Transducers," Electronics Letters, Vol. 6, No. 13, pp. 398-399, Jun. 25, 1970, the disclosure of which is hereby incorporated by reference herein. The various layers can be modeled as one-dimensional elements, with the only dimension corresponding to the dimension in the forward-to-rearward direction of the stack, i.e., the radial dimension in the embodiment of FIGS. 19-22. More precise optimization can be provided by finite element analysis and/or physical modeling and testing. In the emitter of FIGS. 25-28, the liquid in space or passageway 1740 forms an integral part of the resonant unit.

The inner support tube provides a passage through the emitter for catheters, guidewires or other elements of the apparatus. The inner support tube, and any elements disposed within it, are effectively isolated from the ultrasonic vibrations in the resonant unit by reflective interface 1713, and therefore do not affect performance of the emitter.

The optimum dimensions will vary with the desired operating frequency and with the materials employed. However, one exemplary embodiment uses a tubular piezoelectric element made from a ceramic lead zirconate-titanate composition, known in the art by the designation "PZT-8." The tubular transducer has an internal diameter of 83 mils (0.083 inches; 2.1 mm) and a wall thickness of 10.5 mils (0.27 mm), so that the outer diameter of the piezoelectric element is 103 mils (2.6 mm). The outer diameter of outer support tube 1714 is 72 mils (1.8 mm); and the annular passageway 1740 has a radial thickness of 5.5 mils (0.14 mm). The outer support tube is formed from half-hard brass and has a wall thickness of 5 mils (0.13 mm). The dimension between shoulders 1720 and 1722 is 325 mils (8.25 mm), and the effective length of the transducer is 8 mm. This transducer provides peak efficiency at a driving frequency of 9 MHz. When operated at 9 MHz, the transducer provides over fifty percent (50%) efficiency at electrical power levels between 20 and 100 watts. When cooled by water flowing at a rate of a few ml per minute, the transducer has been operated for periods of several minutes or more at power levels up to 100 watts to provide approximately 51 watts of radiated acoustic power.

Figure 24:
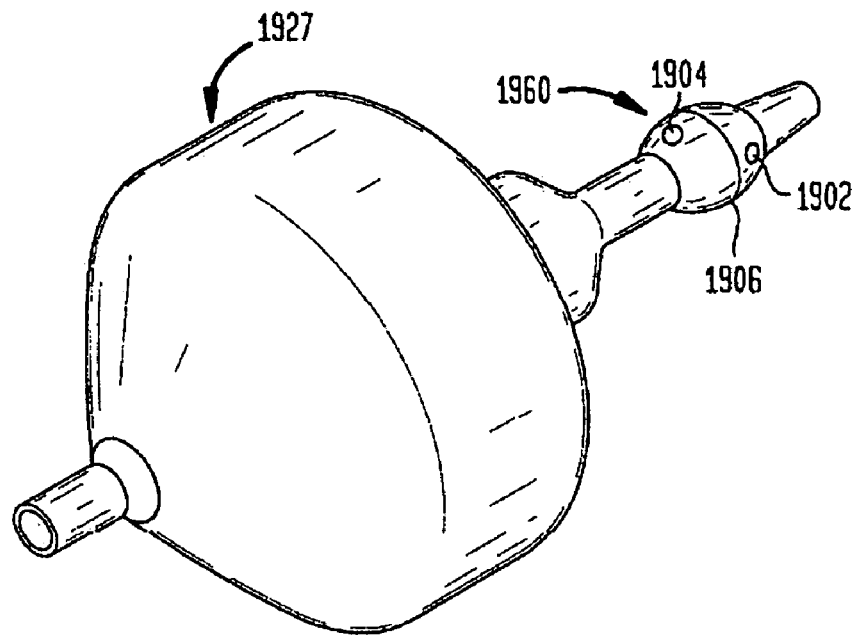
FIGS. 24 and 25 are perspective view of apparatus according to a further embodiment of the invention.
Figure 25:
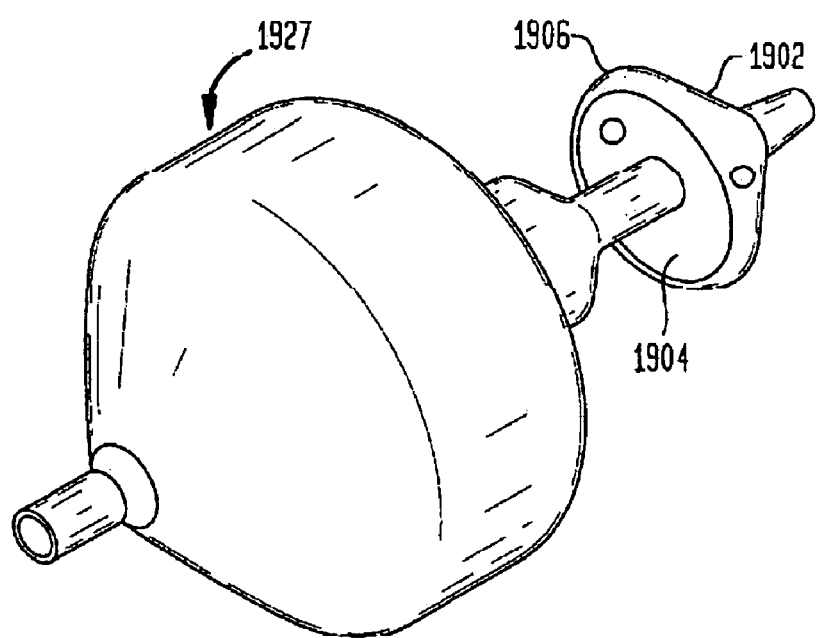

In the embodiment discussed above with reference to FIG. 1, an expansible anchor 62 is provided distal to the expansible reflector structure on a guide catheter extending through the reflector structure. In a further variant of this approach, the anchor may be used to exert a distally-directed force on the expansible reflector structure, so as to urge the expansible reflector structure forwardly. As shown in FIG. 24, an expansible anchor balloon 1960 includes a readily-distensible distal portion 1902 and a less readily-distensible proximal portion 1904. These portions join one another at boundary 1906 encircling the anchor balloon. For example, the less readily-distensible rear portion may be formed from a relatively thick elastomer or an elastomer of relatively high durometer, whereas the more readily-distensible portion may be formed from a thin, low durometer elastomer. When the balloon is positioned in a tubular anatomical structure such as a pulmonary vein or other vascular structure and inflated, the balloon inflates unevenly. The less-distensible rear portion tends to form a flat disk, whereas the more-distensible distal portion expands into a generally conical shape. Thus, during the inflation process, the axial or proximal-to-distal extent of the less-distensible proximal portion 1904 decreases as this portion is transformed to the disk-like shape. During the inflation process, the region of the anchor balloon adjacent boundary 1906 engages the anatomical structure. Thus, as the axial extent of proximal portion 1904 decreases, the proximal portion tends to pull reflector structure 1927 in the distal direction. This pulling action avoids the need for the physician to urge the reflector structure distally during the procedure and allows the use of a highly flexible probe structure, such as a highly flexible carrier catheter. A similar pulling action can be provided by a separate operable element such as a bellows or a thermally-actuated contractile element such as a shape-memory alloy element, mechanically connected between an expansible anchor engagable in the tubular structure or pulmonary vein, and the reflector structure.

The apparatus discussed above can be placed within the internal organ by conventional surgical techniques. For example, where the apparatus is used for ablation of the heart, the apparatus can be introduced into the heart by performing open-heart surgery. However, it is highly desirable to avoid the need for such procedures by placing the apparatus through the vascular system. It is preferred to introduce the apparatus into the heart through the superior or inferior vena cava, then through the right atrium and through the fossa ovalis into the left atrium. Other conventional instruments for treatment of the heart are introduced in this manner, using conventional techniques for guiding and placing elongated probes. Such conventional techniques can be employed for placing the device according to the present invention. For example, a sheath or introducer catheter carrying the device may itself be an actively-steerable device or a "torqueable" device capable of transmitting twisting motions. The carrier catheter carrying the reflective structure may itself be an actively-steerable or torqueable device. Similarly, a guide wire or guide catheter extending through the carrier catheter may be steerable or torqueable. The carrier catheter may be directed within the left atrium by means of a pre-shaped introducer catheter inserted through a sheath. The sheath maintains the introducer catheter in a straight condition as the introducer catheter is advanced through the sheath. When the distal end of the introducer catheter emerges from the sheath within the left atrium, the distal end of the introducer catheter assumes its pre-curved shape. The carrier catheter and expansible structure are advanced through the introducer catheter and directed by the introducer catheter to the appropriate location within the atrium. An introducer catheter, or the carrier catheter itself, may be provided with a deflection wire extending along a portion of the catheter. The distal end of the deflection wire is fixed to a point on the catheter, so that the catheter can be deflected by pulling the wire. These and other conventional placement and steering mechanisms can be used.

The apparatus and methods can be used to treat other cardiac arrhythmias, as by ablating a path around a focus of the arrhythmia. Also, the apparatus and methods can be used for purposes other than ablation of tissues of the heart and circulatory vessels. For example, any cavernous internal organ can be treated in a manner similar to the heart to ablate the wall of such an organ. In a condition referred to as gastroesophageal reflux disease or "GERD," abnormal tissues within the esophagus or stomach may be treated by positioning apparatus as discussed above within the stomach and/or within the esophagus and ablating the abnormal tissue. Also, the techniques discussed above can be used to treat tissues tubular anatomical structures as, for example, structures of the digestive system, respiratory system or urinary system. For example, apparatus similar to that discussed above with reference to FIG. 15, which directs the applied ultrasonic energy in a generally conical pattern, can be employed to treat benign prostatic hyperplasia ("BPH"). In this condition, the prostate gland surrounding the urethra in a male subject swells and tends to constrict the urethra. The apparatus may be inserted into the urethra and ultrasonic energy may be directed into a ring-like focal region outside of the urethra, within the surrounding prostatic tissue so as to ablate the prostate and relieve the swelling. The radial distance from the central axis of the apparatus to the focal region may be selected so as to place the focal region either within the prostate itself or within the capsule surrounding the prostate.

Also, the apparatus and methods discussed above can be used to perform thermal treatments other than ablation. For example, hyperthermia can be applied to potentiate the action of a drug or other agent in a particular region of the body.

The particular fluids and other materials mentioned above can be replaced by other materials having similar properties. For example, the gas/liquid interface used as a reflective interface can be replaced by an interface of any two fluids having markedly different acoustic impedance. In a further variant, the configuration of the reflective active region, or the configuration of an inflatable lens, can be varied by varying the inflation pressures within the various balloons. To provide greater variation in configuration with variations in pressure, more readily distensible materials such as elastomeric materials may be used to form the reflective or refractive regions of the balloons. In yet another variant, the focal length of an inflatable lens can be adjusted while maintaining the shape of the lens constant by varying the composition of the fluid in the lens or the fluid in a surrounding balloon. For example, in the embodiment of FIG. 4, such variation can be employed to adjust the axial position of the focal region and hence the depth of the focal region in the cardiac wall.

In the arrangements discussed above, the liquid used to inflate the structural balloon can also serve as a temperature control medium. The liquid source is arranged to provide the liquid at a desired temperature. This assures that the temperature at the interface between the structural balloon and the tissue will remain substantially at a desired temperature. Stated another way, the boundary condition at the wall of the anatomical structure is well controlled. The controlled temperature may be below normal body temperature to keep the interface cool and minimize or prevent ablation of epithelial cells lining the heart. Conversely, a higher boundary temperature will promote ablation at and near the surface of the heart wall abutting the forward wall in the focal region. To maximize this effect, the fluid in the structural balloon may be maintained just below the temperature which will cause tissue damage independently of the ultrasonic energy as, for example, up to about 41° C.

The structures discussed above with respect to application of ultrasonic energy can be used for imaging as well as for thermal treatment. In one such embodiment, an elongated ultrasonic transducer such as the transducer 20 of FIG. 1 is provided as a series of independently operable rings spaced along the axis of the catheter. Each ring serves both as an emitter and as a detector. The reflector structure may have an active region with a conical shape, so as to redirect radially-directed energy from the rings in the axial or forward direction. Such a structure provides the same effect as a disk-like transducer having multiple independently-operable concentric elements, to form a forwardly-directed imaging beam. However, because the reflector structure is collapsible, the structure in accordance with this embodiment of the invention can be inserted more readily into the body of a living subject or into another confined space. In a further variant, the transducer, or each ring of a transducer with axially-spaced rings, can be subdivided into plural elements spaced circumferentially around the axis of the transducer.

The structures and methods disclosed herein which facilitate positioning, collapse and withdrawal of the expansible balloons used in the reflective structure also can be used to in connection with balloons for other purposes as, for example, in angioplasty.

Also, the apparatus and methods discussed above can be used for purposes other than treatment of living subjects. For example, the balloon reflector structures discussed above can be used in application of ultrasonic energy for many purposes.

As these and other variations and combinations of the features discussed above can be employed, the foregoing description of the preferred embodiments should be taken by way of illustration rather than by way of limitation of the invention.

The invention claimed is:

1. A method of applying energy to the wall of an internal organ of a living subject comprising the steps of:
    (a) positioning an expansible structure within the body of the subject in or adjacent to said organ and bringing said expansible structure to an expanded condition; and
    (b) directing energy onto an active region of said expansible structure so that energy is reflected from said active region and directed from said active region onto the wall of the internal organ, said expansible structure focusing said energy so that energy reflected from the active region is focused in a focal region.

2. A method as claimed in claim 1, wherein said energy reflection at said active region focuses said energy.

3. A method as claimed in claim 1, wherein the energy is directed onto said active region so that the energy is directed into a treatment region of the wall of said organ in the form of an elongated path extending along the wall of said organ.

4. A method as claimed in claim 3 wherein the energy is directed so that said focal region extends along said path within the organ wall at a depth from the surface of the organ wall.

5. A method as claimed in claim 1, wherein said expansible structure includes a first balloon, said step of bringing said reflector structure to said expanded configuration including inflating said first balloon.

6. A method as claimed in claim 5, wherein said first balloon defines a transmissive wall, said positioning step including positioning said first balloon so that said transmissive wall lies adjacent the wall of the organ, and said energy is directed onto said active region from within said first balloon so that the energy is reflected at said active region through the interior of the first balloon and through the transmissive wall into said focal region.

7. A method as claimed in claim 6, wherein said positioning step includes positioning the first balloon so that the transmissive wall lies adjacent the wall of the organ.

8. A method as claimed in claim 7, wherein said positioning step includes positioning the first balloon so that the transmissive wall is spaced from the wall of the organ and maintaining a layer of liquid between the transmissive wall and the wall of the organ, whereby energy directed through the transmissive wall passes through the layer of liquid.

9. A method as claimed in claim 8, wherein said step of inflating said first balloon includes inflating said first balloon with a biocompatible inflation liquid and said step of maintaining a layer of liquid includes discharging the inflation liquid to the exterior of the first balloon so that at least some of the discharged inflation liquid passes between the transmissive wall and the wall of the organ.

10. A method as claimed in claim 5, wherein said positioning step is performed so as to position said first balloon within a chamber of the heart and said path along a wall of the heart, and wherein said energy ablates tissue in the wall of the heart so as to form a first conduction block extending along said elongated path.

11. A method as claimed in claim 10, wherein said positioning step is performed so as to position said first balloon within a chamber of the heart and said path extends along the wall of the heart and at least partially around a first ostium of a first blood vessel communicating with such chamber.

12. A method as claimed in claim 11, wherein said first blood vessel is a pulmonary vein, said first ostium being disposed adjacent an opening of an atrial appendage, the method further comprising forming a second conduction block extending at least partially around the opening of the atrial appendage so that first and second conduction blocks cooperatively encompass and isolate a region of the heart wall including said first ostium and said opening of said atrial appendage.

13. A method as claimed in claim 11, wherein said path is substantially in the form of a closed loop encircling said first ostium.

14. A method as claimed in claim 3, wherein said step of directing energy is performed so as to direct the energy into said focal region along substantially the entire elongated path simultaneously.

15. A method as claimed in claim 1, wherein said energy-directing step includes directing the energy through an inflatable lens and varying the configuration of said inflatable lens so as to vary the location of said focal region.

16. A method as claimed in claim 1, wherein said energy-directing step includes directing the energy from a source to said active region and varying the positional relationship between said source and said active region so as to vary the location of said focal region.

17. A method as claimed in claim 1, wherein said step of directing energy onto said active region includes directing ultrasonic energy through a first fluid having a first acoustic impedance and onto an interface at said active region between said first fluid and a second fluid having a second acoustic impedance different from said first acoustic impedance.

* * * * *